United States Patent
Bamber et al.

(10) Patent No.: US 10,674,920 B2
(45) Date of Patent: Jun. 9, 2020

(54) ULTRASONIC IMAGING

(71) Applicants: THE INSTITUTE OF CANCER RESEARCH: ROYAL CANCER HOSPITAL, London (GB); UNIVERSITY OF BERN, Bern (CH)

(72) Inventors: Jeffrey Colin Bamber, Sutton (GB); Martin Frenz, Bern (CH); Michael Jaeger, Bern (CH)

(73) Assignees: THE INSTITUTE OF CANCER RESEARCH: ROYAL CANCER HOSPITAL, London (GB); UNIVERSITY OF BERN, Bern (CH)

( * ) Notice: Subject to any disclaimer, the term of this patent is extended or adjusted under 35 U.S.C. 154(b) by 158 days.

(21) Appl. No.: 14/417,427

(22) PCT Filed: Jul. 24, 2013

(86) PCT No.: PCT/GB2013/051983
§ 371 (c)(1),
(2) Date: Jan. 26, 2015

(87) PCT Pub. No.: WO2014/016600
PCT Pub. Date: Jan. 30, 2014

(65) Prior Publication Data
US 2015/0182122 A1    Jul. 2, 2015

(30) Foreign Application Priority Data

Jul. 26, 2012  (GB) .................................. 1213304.7

(51) Int. Cl.
*A61B 5/00*    (2006.01)
*A61B 8/08*    (2006.01)
(Continued)

(52) U.S. Cl.
CPC .......... *A61B 5/0095* (2013.01); *A61B 5/7225* (2013.01); *A61B 8/02* (2013.01);
(Continued)

(58) Field of Classification Search
CPC ... A61B 5/0095; A61B 8/5246; A61B 8/5269; A61B 8/485; A61B 8/02; A61B 8/4416;
(Continued)

(56) References Cited

U.S. PATENT DOCUMENTS

2005/0015009 A1*  1/2005  Mourad ................. A61B 5/031
                                                                600/438
2009/0069674 A1*  3/2009  Masumura ........... A61B 5/0073
                                                                600/425
2009/0203997 A1   8/2009  Ustuner

FOREIGN PATENT DOCUMENTS

WO    WO 2009/063424    5/2009

OTHER PUBLICATIONS

Jaeger et al., "Reduction of background in optoacoustic image sequences obtained under tissue deformation," Journal of Biomedical Optics, 2009, vol. 14(5), pp. 054011-1-054011-10.
(Continued)

*Primary Examiner* — Bo Joseph Peng
(74) *Attorney, Agent, or Firm* — Sheridan Ross P.C.

(57) ABSTRACT

A method of imaging a region of interest of a body, the body having sites outside the region which can produce image clutter. The method includes: generating a first pattern of vibration within the body to produce a localised first displacement at the region and localised first displacements at the clutter-producing sites; while the body undergoes the first displacements, generating ultrasound signals from the region, and detecting the ultrasound signals to generate a first image of the region; generating a second pattern of vibration within the body to produce a localised second
(Continued)

displacement at the region and localised second displacements at the clutter-producing sites; while the body undergoes the second displacements, generating ultrasound signals from the region, and detecting the ultrasound signals to generate a second image of the region; and combining the first and second images to produce a third image of the region. The first and second vibration patterns are selected such that the first and second displacements combine in the production of the third image to reduce or eliminate the clutter in the third image relative to the clutter in the first and second images.

26 Claims, 5 Drawing Sheets

(51) Int. Cl.
    *A61B 8/00*         (2006.01)
    *A61B 8/02*         (2006.01)
    *G06T 7/00*         (2017.01)

(52) U.S. Cl.
    CPC ............ *A61B 8/4416* (2013.01); *A61B 8/485* (2013.01); *A61B 8/5246* (2013.01); *A61B 8/5269* (2013.01); *G06T 7/0012* (2013.01); *A61B 5/0035* (2013.01); *A61B 5/0066* (2013.01); *G06T 2207/10132* (2013.01)

(58) Field of Classification Search
    CPC ... A61B 5/7225; A61B 5/0066; A61B 5/0035; G06T 7/0012; G06T 2207/10132
    See application file for complete search history.

(56) References Cited

OTHER PUBLICATIONS

Shiina et al., "Real Time Tissue Elasticity Imaging Using the Combined Autocorrelation Method," J Med Ultrasonics, 2002, vol. 29(Autumn), pp. 119-128.
Melodelima et al., "Transient Elastography Using Impulsive Ultrasound Radiation Force: A Preliminary Comparison with Surface Palpation Elastography," Ultrasound in Med. & Biol., 2007, vol. 33(6), pp. 959-969.
Jaeger et al., "Clinical Demonstration of Epi-Mode Photoacoustic Clutter Reduction Using Palpation Scanning," IEEE International Ultrasonics Symposium Proceedings, 2011, pp. 2360-2363.
Jaeger et al., "Clinical Feasibility of Duplex Photoacoustic and Ultrasound Pulse-Echo Imaging Using Photoacoustic Transmit Pulses," IEEE International Ultrasonics Symposium Proceedings, 2011, pp. 304-307.
Jaeger et al., "Deformation-compensated averaging for clutter reduction in epiphotoacoustic imaging in vivo," Journal of Biomedical Optics, 2012, vol. 17(6), pp. 066007-1-06607-8, 9 pages.
Bamber et al., "EFSUMB Guidelines and Recommendations on the Clinical Use of Ultrasound Elastography. Part 1: Basic Principles and Technology," Ultraschall in Med, A52013, vol. 34, pp. 169-184, 19 pages.
Jaeger et al., "Clutter elimination for deep clinical optoacoustic imaging using localised vibration tagging (LOVIT)," Photoacoustics 1, 2013, pp. 19-29.
Shiina et al., "WFUMB Guidelines and Recommendations for Clinical Use of Ultrasound Elastography: Part 1: Basic Principles and Terminology," Ultrasound in Medicine and Biology, 2015, vol. 41(5), pp. 1126-1147.
Bu et al., "Adaptive Depth Compensation Algorithm for Photoacoustic Tomography," 2010, IEEE International Ultrasonics Symposium Proceedings, 2010, pp. 2139-2142.
Held et al., "Effect of irradiation distance on image contrast in epi-optoacoustic imaging of human volunteers," Biomedical Optics Express, 2014, vol. 5(11), pp. 3765-3780.
Jaeger et al., "Improved contrast deep optoacoustic imaging using displacement-compensated averaging: breast tumour phantom studies," Physics in Medicine and Biology, 2011, vol. 56, pp. 5889-5901, 14 pages.
Jaeger et al., "Fourier reconstruction in optoacoustic imaging using truncated regularized inverse k-space interpolation," Inverse Problems, 2007, vol. 23, pp. S51-S63.
Jaeger et al., "Iterative Reconstruction Algorithm for Reduction of Echo Background in Optoacoustic Images," SPIE Proceedings, 2008, vol. 6856, 15 pages.
Frenz et al., "Optimization of tissue irradiation in optoacoustic imaging using linear transducer: theory and experiments," SPIE Proceedings, 2008, vol. 6856 68561Y-1, 13 pages.
Nightingale et al., "Acoustic Radiation Force Impulse Imaging: In Vivo Demonstration of Clinical Feasibility," Ultrasound in Medicine & Biology, 2002, vol. 28(2), pp. 227-235, 10 pages.
Kim et al., "Photoacoustic imaging platforms for multimodal imaging," Ultrasonography, 2015, vol. 34, pp. 88-97.
Lediju et al., "A Motion-Based Approach to Abdominal Clutter Reduction," IEEE Trans Ultrason Ferroelectr Freq Control, 2009, vol. 56(11), pp. 2437-2449, 26 pages.
Lediju et al., "Quantitative Assessment of the Magnitude, Impact and Spatial Extend of Ultrasonic Clutter," Ultrason Imaging, 2008, vol. 30(3), pp. 151-168, 23 pages.
Podoleanu, "Optical coherence tomography," Journal of Microscopy, 2012, 11 pages.
Yao et al., "Breakthrough in Photonics 2013: Photoacoustic Tomography in Biomedicine," IEEE Photonics J., 2014, vol. 6(2), 10 pages.
Zackrisson et al., "Light In and Sound Out: Emerging Translational Strategies for Photoacoustic Imaging," Cancer Res., 2014, vol. 74(4), pp. 979-1004, 45 pages.
International Search Report and Written Opinion for International (PCT) Patent Application No. PCT/GB2013/051983, dated Nov. 26, 2013, 12 pages.
International Preliminary Report on Patentability for International (PCT) Patent Application No. PCT/GB2013/051983, dated Jan. 27, 2015, 9 pages.

\* cited by examiner

ULTRASONIC IMAGING

CROSS REFERENCE TO RELATED APPLICATIONS

This application is a national stage application under 35 U.S.C. 371 and claims the benefit of PCT Application No. PCT/GB2013/051983 having an international filing date of Jul. 24, 2013, which designated the United States, which PCT application claimed the benefit of Great Britain Patent Application No. 1213304.7 filed Jul. 26, 2012, the disclosures of each of which are incorporated herein by reference in their entirety.

FIELD OF THE INVENTION

The present invention relates to a method and a system for ultrasonic imaging, and in particular for reducing or eliminating clutter in photoacoustic and other types of ultrasonic images.

BACKGROUND OF THE INVENTION

In photoacoustic (PA) imaging, tissue irradiation using light (typically pulsed laser light), and subsequent thermoelastic conversion of absorbed light to ultrasound, allows the detection of optically absorbing structures deep inside biological tissue with high resolution using ultrasound receive beamforming[1,2]. This technique is especially promising for functional imaging of the vasculature[2], and of the blood oxygenation level using a multi optical wavelength approach based on the different optical absorption spectra of oxy- and deoxyhaemoglobin[3]. Photoacoustic imaging therefore holds promise for the diagnosis of vascular diseases and cancer[4] and monitoring response to treatment[5,6]. In addition, gold nanoparticles, tailored to strongly absorb light in the NIR range, can serve as contrast media[7,8], and their functionalisation for specific chemical targets allows early detection of e.g. cancer and atherosclerosis Potentially, PA methods can provide an additional functional imaging modality, augmenting conventional ultrasound (US), for example in a real-time, safe, cheap, and versatile multimodal device for improved clinical diagnostics. For versatile imaging of the human body, an epi-style setup is preferred, combining the optical components with the acoustic probe for optical irradiation of the tissue from the same body surface as acoustic signal detection. In this way the influence of bones, acoustically attenuating tissue, and gas on ultrasound propagation from the illuminated tissue region to the acoustic probe can be reduced.

An important requirement for a clinically adequate and thus successful combination of PA and US imaging is an imaging depth of several centimetres, which is feasible in theory taking into account optical attenuation and transducer noise [°]. Such an imaging depth has, however, been difficult to achieve in practice. A reason is that the epiphotoacoustic setup causes severe clutter, which degrades contrast and limits imaging to depths considerably less than the noise-limited theoretical depth, at typically one centimetre or even less[10,11]. Clutter can emerge from strong PA transients that are generated at the site of tissue irradiation close to the ultrasound probe, where optically absorbing structures such as melanin and the microvasculature are exposed to the greatest intensity of irradiating light, or potentially elsewhere if a strong enough PA signal is generated. These transients obscure weak signals from deep inside the tissue when propagating directly to the acoustic receiver (direct clutter), and to the acoustic receiver via acoustic scattering from echogenic structures when propagating into the tissue (echo clutter).

Deep clinical PA imaging thus requires methods for clutter reduction to achieve the theoretical depth of several centimetres. For this purpose, displacement-compensated averaging (DCA) was previously developed[11-13], a technique exploiting the clutter decorrelation that naturally occurs when palpating the tissue with the ultrasound probe, in motions parallel to the imaging plane. When compensating the resulting PA image sequence for the local relative tissue displacement, the "true" PA signal remains well registered and correlated whereas clutter decorrelates and can be reduced by averaging. DCA takes advantage of a combined PA and US system, because US speckle tracking provides the knowledge of local tissue displacement required for DCA.

Evaluation of DCA in combined PA and US imaging of human volunteers has demonstrated that clutter is an actual issue in clinical imaging, and that clutter reduction is feasible[13]. DCA, however, shows several disadvantages at the clinical application level. First, it can only be employed for easily palpable tissue such as breast and limb muscles, and requires a considerable amount of practice for controlled palpation in a free-hand approach. More significantly, however, is its limited clutter reduction and hence image contrast gain, determined by the maximum achievable tissue deformation on one side and by the minimum deformation required for clutter decorrelation on the other side. This typically results in a contrast gain not larger than three[12], whereas a significantly larger contrast gain is desirable to achieve strongly increased imaging depth down to the noise limit.

Similar problems of clutter-limited image contrast exist in conventional US imaging, and potentially other forms of imaging such as optical coherence tomography (OCT). In conventional US echography, acoustic clutter may, for example, arise from acoustic scatterers interacting with side lobes or grating lobes, which may generate clutter echoes that return to the acoustic receiver either directly or after being scattered by other echogenic structures, or reverberation of ultrasound between acoustic scatterers that are proximal to the depth of interest[13b]. Approaches that are similar to DCA have been developed for US pulse-echo imaging independently and apparently without awareness of those developed for PA imaging, and perform with similar limitations to DCA in PA imaging[13c]. In OCT the strong and multiple optical scattering by tissue may generate substantial optical clutter. In the most common form of OCT this is substantially reduced by the use of a highly collimated beam of light[13d]. However, not only does this not fully remove the possibility of optical clutter generation at depths where the beam has been diffused by scattering, it has the substantial disadvantage that to produce an OCT image this beam must be scanned, reducing image frame rate. Alternative parallel acquisition methods using large area detectors offer potential for high frame and volume rate imaging but suffer from poor, optical clutter-limited, image contrast DCA methods may well be applicable to OCT and other imaging methods, although do not appear to have been tried and can be expected to perform with similar limitations to their performance in PA and US imaging.

Accordingly, for PA, US, OCT and other forms of imaging, an alternative approach to reducing or eliminating clutter is required.

SUMMARY OF THE INVENTION

In general terms, the present invention provides a method in which vibration-induced localised displacements, as opposed to the quasi-static deformation in DCA, "tag" the ultrasound signal at the place of origin, enabling the unambiguous identification of this signal and, in theory, full clutter cancellation.

In a first aspect, the present invention provides a method of imaging a region of interest of a body, the body having sites outside the region which can produce image clutter, the method including:

generating a first pattern of vibration within the body to produce a localised first displacement at the region and localised first displacements at the clutter-producing sites;

while the body undergoes the first displacements, generating ultrasound signals from the region, and detecting the ultrasound signals to generate a first image of the region;

generating a second pattern of vibration within the body to produce a localised second displacement at the region and localised second displacements at the clutter-producing sites;

while the body undergoes the second displacements, generating ultrasound signals from the region, and detecting the ultrasound signals to generate a second image of the region; and combining the first and second images to produce a third image of the region;

wherein the first and second vibration patterns are selected such that the first and second displacements combine in the production of the third image to reduce or eliminate the clutter in the third image relative to the clutter in the first and second images.

The third image can conveniently be a difference image of the first and second images. For example, one option is to select one of the first or second vibration patterns such that it produces substantially the same predetermined displacement at the region and the clutter-producing sites. In this case, the other of the first or second vibration patterns can be selected such that it also produces the same predetermined displacement at the clutter-producing sites, but produces a different displacement at the region. Such a selection of vibration patterns can facilitate difference image production.

According to the above option, the predetermined displacement can be a zero displacement. However, more generally it is possible to generate one of the images without a corresponding vibration pattern at all. Thus, in a second aspect, the present invention provides a method of imaging a region of interest of a body, the body having sites outside the region which can produce image clutter, the method including:

generating a pattern of vibration within the body to produce a non-zero localised displacement at a first location which is one of (A) the region and (B) the clutter-producing sites and substantially no displacement at a second location which is the other of (A) the region and (B) the clutter-producing sites;

while the first location undergoes the displacement, generating ultrasound signals from the region, and detecting the ultrasound signals to generate a first image of the region;

in the absence of displacement at the region and the clutter-producing sites, generating ultrasound signals from the region, and detecting the ultrasound signals to generate a second image of the region;

combining the first and second images to produce a third image of the region, the clutter in the third image being reduced or eliminated relative to the clutter in the first and second images.

Again, conveniently, in the method of the second aspect, the third image produced by combining the first and second images can be a difference image. In particular, the difference image approach can be facilitated by having the first location as (A) the region.

In the first or second aspect, each non-zero localised displacement is a transient or dynamic localised displacement produced by the respective vibration pattern. In contrast, DCA does not produce such transient or localised displacements but relies instead on quasi-static tissue displacement and deformation of the entire tissue produced by tissue palpation.

Advantageously, the methods of the first and second aspects enable clutter reduction or elimination without a need for such palpation. The methods of the first and second aspects also work in a fundamentally different way to DCA; DCA distinguishes clutter from required signal, and produces clutter reduction, by using differences in global deformation-induced decorrelation of the image structure, whereas in the methods of the above aspects the localised and dynamic nature of the induced displacement allows "tagging" or coding of either the generated ultrasound signal in the region of interest or the clutter, so as to be able to distinguish between the two. In the second aspect, for example, when the first location is (B) the clutter-producing sites the method can not only facilitate clutter reduction but can allow the source of clutter to be identified as located at the position of vibration tagging that maximises clutter reduction. Such an outcome is not possible with DCA.

In a third aspect, the present invention provides a method of imaging a body including:

repeatedly performing the method either the first or the second aspect for different regions of interest of the body; and combining the third images from the repeat performances to build up a composite image of the body.

In a fourth aspect, the present invention provides a system for imaging a region of interest of a body, the body having sites outside the region which can produce image clutter, the system including:

(i) an apparatus for (a) generating a pattern of vibration within the body to produce a localised displacement at the region and localised displacements at the clutter-producing sites, (b) while the body undergoes the displacements, generating ultrasound signals from the region, and (c) detecting the ultrasound signals to generate an image of the region; and (ii) a computer system which controls the apparatus to: either (a) generate a first pattern of vibration within the body to produce a localised first displacement at the region and localised first displacements at the clutter-producing sites; while the body undergoes the first displacements, generate ultrasound signals from the region, and detect the ultrasound signals to generate a first image of the region; generate a second pattern of vibration within the body to produce a localised second displacement at the region and localised second displacements at the clutter-producing sites; while the body undergoes the second displacements, generate ultrasound signals from the region, and detect the ultrasound signals to generate a second image of the region; or (b) generate a pattern of vibration within the body to produce a non-zero localised displacement at a first location which is one of (A) the region and (B) the clutter-producing sites and substantially no displacement at a second location which is the other of (A) the region and (B) the clutter-producing sites; while the first location undergoes the displacement, generate ultrasound signals from the region, and detect the ultrasound signals to generate a first image of the region; in the absence of displacement at the region and the clutter-producing sites, generate ultrasound signals from the region, and detect the ultrasound signals to generate a second image of the region;

wherein the computer system further combines the first and second images to produce a third image of the region, the clutter in the third image being reduced or eliminated relative to the clutter in the first and second images. The system may further include one or more displays for displaying the images.

In a fifth aspect, the present invention provides the computer system of the fourth aspect.

In a sixth aspect, the present invention provides a computer program comprising code which, when run on a computer, causes the computer to control an apparatus for (a) generating a pattern of vibration within the body to produce a localised displacement at the region and localised displacements at the clutter-producing sites, (b) while the body undergoes the displacements, generating ultrasound signals from the region, and (c) detecting the ultrasound signals to generate an image of the region;

the computer program controlling the apparatus to: either (a) generate a first pattern of vibration within the body to produce a localised first displacement at the region and localised first displacements at the clutter-producing sites; while the body undergoes the first displacements, generate ultrasound signals from the region, and detect the ultrasound signals to generate a first image of the region; generate a second pattern of vibration within the body to produce a localised second displacement at the region and localised second displacements at the clutter-producing sites; while the body undergoes the second displacements, generate ultrasound signals from the region, and detect the ultrasound signals to generate a second image of the region; or (b) generate a pattern of vibration within the body to produce a non-zero localised displacement at a first location which is one of (A) the region and (B) the clutter-producing sites and substantially no displacement at a second location which is the other of (A) the region and (B) the clutter-producing sites; while the first location undergoes the displacement, generate ultrasound signals from the region, and detect the ultrasound signals to generate a first image of the region; in the absence of displacement at the region and the clutter-producing sites, generate ultrasound signals from the region, and detect the ultrasound signals to generate a second image of the region;

wherein the computer program further comprises code which combines the first and second images to produce a third image of the region, the clutter in the third image being reduced or eliminated relative to the clutter in the first and second images.

In a seventh aspect, the present invention provides a computer readable medium storing the computer program of the sixth aspect.

Each of: the system of the fourth aspect, the computer system of the fifth aspect, the computer program of the sixth aspect, and the computer readable medium of the seventh aspect can be used to perform the method of any one of the first to third aspects. Thus for example, in relation to the third aspect, the computer system of the fourth or fifth aspect, and/or the computer program of the sixth or seventh aspect may further control the apparatus to generate first and second images for different regions of interest of the body, combine the first and second images for the different regions to produce respective third images of the regions, and combine the third images to build up a composite image of the body.

Further optional features of the invention of the first to seventh aspects will now be set out. Unless otherwise stated, these are applicable singly or in any combination with any aspect of the invention of the first to seventh aspects.

In general, the longest duration of the transient displacement that would be produced by the vibration pattern or, correspondingly, the lowest useful temporal frequency of vibration, can be determined by the requirement to be able to identify the locality of the vibration at any moment, and this is in turn can be determined by, amongst other things, the speed with which the dynamic tissue deformation induced by the vibration is propagated away from the intended location. Such speed may be that of a shear wave, Rayleigh wave, Lamb wave, or other wave, the type of wave being determined by the mode of propagation that dissipates the energy of the vibration to locations in the tissue other than the imaged region or the clutter region. For example, frequencies used in the current medical imaging methods of transient elastography[13e], shear wave elastography[13f], and acoustic radiation force impulse imaging[14] which are in the region of 50 Hz to 1200 Hz, may provide sufficient spatial localisation, the higher the frequency the better, although this does not exclude the use of frequencies outside this range. Thus, the or each localised displacement may be caused by a vibration having a frequency of at least 50 Hz.

The imaging of the region of interest can be performed using photoacoustic imaging. Thus the ultrasound signals can be generated from the region optically by irradiating the region using light, which is typically pulsed light such as pulsed laser light. Alternatively, the imaging of the region of interest can be performed using e.g. echo ultrasound, optical coherence tomography or another imaging technique.

The imaging of the region of interest can be performed by epi-acoustic imaging, in which the procedure to generate the ultrasound signals (i.e. the optical irradiation in the case of epiphotoacoustic imaging), and the ultrasound signal detection are performed from the same surface of the body.

The method may be a method of photoacoustically imaging in which the optical irradiation and the ultrasound signal detection are performed from different locations outside or inside the body.

The body may be a human or animal body, or a part thereof.

The first and the second images may each be generated by combining a plurality of sequentially acquired image frames. In this way the signal to noise ratio (SNR) of the images can be improved. Conveniently, during their sequential acquisition, the image frames of the first image may be interleaved with the image frames of the second image.

The method may further include: generating one or more further patterns of vibration within the body to produce, for each further pattern, a localised further displacement at the region and localised further displacements at the clutter-producing sites; while the body undergoes the further displacements of each further vibration pattern, generating ultrasound signals from the region, and detecting the ultrasound signals to generate a respective further image of the region for each further vibration pattern; and combining the one or more further images with the first and second images to produce the third image of the region. In general, the more images of a region there are available, the more possibilities exist for combining images to reduce or eliminate clutter. In particular, echo clutter may be further reduced in this way.

Although it can be convenient to produce a simple difference image from the first and second images, more sophisticated image production procedures can be adopted, particularly when further images are used to produce the third image. For example, the third image can be produced by solving a system of linear equations corresponding to the first, second and further images. Such a system can include the use of filters and weighted combinations of the first, second and further images derived from techniques such as principle components, multiple discriminant analysis, neural networks, blind source separation and other methods for distinguishing between one vibration tagging/coding (i.e. localised displacement) and another, or between vibration and no vibration.

In general, the vector(s) of the localised displacement(s) produced by the or each vibration pattern may be used to produce the third image, along with the first, second and (optional) further images. In some situations, these vectors may be known or may be calculable from the physical properties of the body and the parameters used to generate the vibration pattern. However, particularly when the body is formed of human or animal tissue, the vectors may not be known or readily calculable. Thus, the method may further include: measuring the vector(s) of the localised displacement(s) produced by the or each vibration pattern. The vectors can be measured using known approaches, such as correlation based tracking of the phase of, or the envelope of, the radio frequency (RF) pulse-echo signal, and/or ultrasound elastography (e.g. when imaging the region using an echo ultrasound imaging system, or using echo ultrasound mode in a combined echo ultrasound and photoacoustic imaging system).

Conveniently, the or each vibration pattern may be generated by the acoustic radiation force of a focused ultrasonic beam. However, other techniques for generating vibration patterns may be adopted. For example, a shear wave can be generated at the surface of the body (e.g. using a vibrating indenter) forming a transient impulsive or harmonic shear wave propagating into the body. Advantageously a single such propagating shear wave can be used as the vibration pattern for the performance of photoacoustic imaging or other types of ultrasonic imaging at respective regions along the path of travel of the propagating wave (i.e. when the propagating shear wave reaches each region along the path, that region can be optically or acoustically irradiated using pulsed light or ultrasound to generate ultrasound signals from the region, and the ultrasound signals can be detected to generate an image of the region). Another option is to generate a vibration pattern by imposing a fluctuating magnetic field on the body to vibrate magnetic particles in the body.

Combination approaches can be envisaged, one example being the combination of multiple different localised transient displacement vectors of different directions, amplitudes and/or frequencies, to improve multivariate discrimination of signal from clutter, another being the combination of multiple different propagating shear waves of either different direction, different source location or different frequency, used with an appropriate "inverse solution" or "synthetic aperture" data processing method to generate each vibration-tagged image.

Conveniently, the same ultrasound imaging probe may be used to detect the ultrasound signals as may be used to generate the respective vibration patter. Such an arrangement can help to align the vibration pattern-forming beam with the image-forming beam. However, another option, particularly when using a focused ultrasonic beam lying in the plane of the images, is for the beam to penetrate the body at an angle relative to the direction of detection of the ultrasound signals.

Efficient image acquisition procedures can be adopted whereby the detected ultrasound signals used to generate an image of a region can be reused to generate images of one or more additional (e.g. neighbouring) regions. By reusing the ultrasound signals in this way, it is possible to build up more quickly a composite image of the body. For example, the first vibration patter and the second vibration pattern may be complimentary and opposite, such that, if the first vibration pattern is superimposed on the second vibration pattern, in the plane of the images the resulting combined localised first and second displacements are uniform or zero across the body. Thus, the first and second vibration patterns could each produce a checkerboard pattern of high amplitude displacement regions and low or zero amplitude displacement regions, one checkerboard pattern being the negative of the other. Such an arrangement can lead to highly efficient image acquisition. In particular, each pattern can be used to generate respective images from its regions which can then be combined with the corresponding images from the other pattern to produce low clutter third images for all the regions.

The computer-readable medium of the seventh aspect includes, but is not limited to, portable or fixed storage devices, wireless channels and other storage mediums capable of storing, containing or carrying instruction(s) and/or data. A storage medium may represent one or more devices for storing data, including read only memory (ROM), random access memory (RAM), magnetic RAM, core memory, magnetic disk storage mediums, optical storage mediums, flash memory devices and/or other machine readable mediums for storing information.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer-readable medium. In the computer system of the fourth or fifth aspect, one or more processor may perform necessary tasks. More generally, another option is to take advantage of naturally occurring tissue motion. If such tissue motion is sufficiently localised and dynamic, as may be the case for small pulsating arteries, it may represent an alternative means of inducing the localised displacements for implementing a passive form of the method, i.e. without actively producing a localised vibration, albeit with the possible disadvantage that clutter reduction can only be achieved at specific (uncontrolled) locations of e.g. identified pulsating blood vessels. Alternatively, cardiac and/or vascular pulsations may act as a source of shear waves, which can then be used for performance of clutter-reduced photoacoustic imaging or other types of ultrasonic imaging at respective regions along the path of travel of the propagating waves.

Thus, in an eighth aspect, the present invention provides a method of imaging a region of interest of a body, the body having sites outside the region which can produce image clutter, and the body undergoing autonomous tissue motion which produces a localised first displacement at the region and localised first displacements at the clutter-producing sites, and which further produces a localised second displacement at the region and localised second displacements at the clutter-producing sites, the method including:

while the body undergoes the first displacements, generating ultrasound signals from the region, and detecting the ultrasound signals to generate a first image of the region;

while the body undergoes the second displacements, generating ultrasound signals from the region, and detecting the ultrasound signals to generate a second image of the region; and combining the first and second images to produce a third image of the region;

wherein the first and second vibration patterns are selected such that the first and second displacements combine in the production of the third image to reduce or eliminate the clutter in the third image relative to the clutter in the first and second images.

Thus the method of the eighth aspect is similar to the method of the first aspect except that the first and second displacements derive from autonomous tissue motion rather than the active generation of patterns of vibration within the body. For example, the autonomous tissue motion may be produced by artery pulsation or by shear waves produced by cardiac and/or vascular pulsations. The first and second displacements can then correlate to different phases in the heart cycle, the artery being in different states of localised displacement, or the shear waves producing different states of localised displacement, at the different phases.

In the eighth aspect, each localised displacement is a transient or dynamic localised displacement produced by the autonomous tissue motion, the localised and dynamic nature of the induced displacement allowing "tagging" or coding of either the generated ultrasound signal in the region of interest or the clutter, so as to be able to distinguish between the two. As previously mentioned, DCA does not produce such transient or localised displacements but relies instead on quasi-static tissue displacement and deformation of the entire tissue produced by tissue palpation. Thus, the method of the eighth aspect, like those of the first and second aspects, enables clutter reduction or elimination without a need for such palpation.

In a ninth aspect, the present invention provides a system for imaging a region of interest of a body, the body having sites outside the region which can produce image clutter, and the body undergoing autonomous tissue motion which produces a localised first displacement at the region and localised first displacements at the clutter-producing sites, and which further produces a localised second displacement at the region and localised second displacements at the clutter-producing sites, the system including:

(i) an apparatus for (a) while the body undergoes the displacements, generating ultrasound signals from the region, and (b) detecting the ultrasound signals to generate an image of the region; and (ii) a computer system which controls the apparatus to: while the body undergoes the first displacements, generate ultrasound signals from the region, and detect the ultrasound signals to generate a first image of the region; while the body undergoes the second displacements, generate ultrasound signals from the region, and detect the ultrasound signals to generate a second image of the region;

wherein the computer system further combines the first and second images to produce a third image of the region, the clutter in the third image being reduced or eliminated relative to the clutter in the first and second images. The system may further include one or more displays for displaying the images.

In a tenth aspect, the present invention provides the computer system of the ninth aspect.

In an eleventh aspect, the present invention provides a computer program comprising code which, when run on a computer, causes the computer to control an apparatus for (a) while the body undergoes the displacements, generating ultrasound signals from the region, and (b) detecting the ultrasound signals to generate an image of the region;

the computer program controlling the apparatus to: while the body undergoes the first displacements, generate ultrasound signals from the region, and detect the ultrasound signals to generate a first image of the region; while the body undergoes the second displacements, generate ultrasound signals from the region, and detect the ultrasound signals to generate a second image of the region;

wherein the computer program further comprises code which combines the first and second images to produce a third image of the region, the clutter in the third image being reduced or eliminated relative to the clutter in the first and second images.

In a twelfth aspect, the present invention provides a computer readable medium storing the computer program of the eleventh aspect.

Each of: the system of the ninth aspect, the computer system of the tenth aspect, the computer program of the eleventh aspect, and the computer readable medium of the twelfth aspect can be used to perform the method of the eighth aspect.

Further optional features of the invention of the eighth to twelfth aspects will now be set out. Unless otherwise stated, these are applicable singly or in any combination with any aspect of the invention of the eighth to twelfth aspects.

The imaging of the region of interest can be performed using photoacoustic imaging. Thus the ultrasound signals can be generated from the region optically by irradiating the region using light, which is typically pulsed light such as pulsed laser light. Alternatively, the imaging of the region of interest can be performed using e.g. echo ultrasound, optical coherence tomography or another imaging technique.

The method may be a method of photoacoustically imaging in which the optical irradiation and the ultrasound signal detection are performed from different locations outside or inside the body.

The body may be a human or animal body, or a part thereof.

The first and the second images may each be generated by combining a plurality of sequentially acquired image frames. In this way the signal to noise ratio (SNR) of the images can be improved. Conveniently, during their sequential acquisition, the image frames of the first image may be interleaved with the image frames of the second image.

The body may undergo autonomous tissue motion which produces one or more further localised displacements at the region and one or more further localised displacements at the clutter-producing sites. The method may then further include: while the one or more further displacements are produced, generating ultrasound signals from the region, and detecting the ultrasound signals to generate one or more respective further images of the region; and combining the one or more further images with the first and second images to produce the third image of the region. For example, the further localised displacements can correlate to further different phases in the heart cycle.

Although it can be convenient to produce a simple difference image from the first and second images, more sophisticated image production procedures can be adopted, particularly when further images are used to produce the third image. For example, the third image can be produced by solving a system of linear equations corresponding to the first, second and further images. Such a system can include the use of filters and weighted combinations of the first, second and further images derived from techniques such as principle components, multiple discriminant analysis, neural networks, blind source separation and other methods for distinguishing between one vibration tagging/coding (i.e. localised displacement) and another, or between vibration and no vibration.

The computer-readable medium of the twelfth aspect includes, but is not limited to, portable or fixed storage devices, wireless channels and other storage mediums capable of storing, containing or carrying instruction(s) and/or data. A storage medium may represent one or more devices for storing data, including read only memory (ROM), random access memory (RAM), magnetic RAM, core memory, magnetic disk storage mediums, optical storage mediums, flash memory devices and/or other machine readable mediums for storing information.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer-readable medium. In the computer system of the ninth aspect, one or more processor may perform necessary tasks.

Further optional features of the invention are set out below.

BRIEF DESCRIPTION OF THE DRAWINGS

Embodiments of the invention will now be described by way of example with reference to the accompanying drawings.

DETAILED DESCRIPTION AND FURTHER OPTIONAL FEATURES OF THE INVENTION

Figure 1:
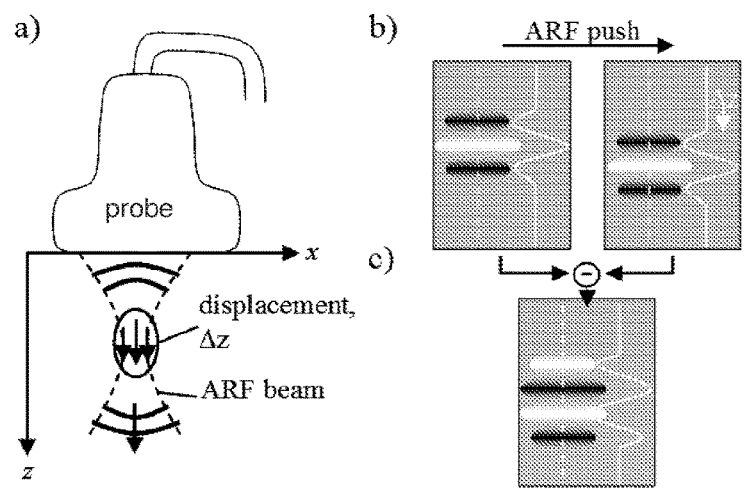
FIG. 1: *a*) Setup with a linear probe used for both imaging and acoustic radiation force (ARF) generation using an ultrasonic focused beam. The z-direction is known as the axial direction, the x-direction as the lateral direction, and y-direction (orthogonal to both the x- and z-directions) as the elevation direction. *b*) The signal from a point absorber is shifted in axial direction when comparing PA images acquired pre and post ARF push. The images show the point-spread function from the point absorber, as well as the axial profile of the PSF along the dashed lines. *c*) In a difference image the signal of the point absorbers has a slightly changed PSF.

In the following the term LOVIT is used to denote the approach of the present invention, in which localised displacements provide vibration tagging of the ultrasound signal (hence LOVIT from localised vibration tagging). These displacements can be induced, among other potential methods, by means of the acoustic radiation force (ARF) generated by an ultrasonic focused beam. A convenient way of implementing ARF is to use an imaging transducer also for transmission of the focused beam. This allows the focused beam to be steered during the transmit phase of the individual transducer elements, generating a transient push in any location which is inherently aligned with the imaging plane. The ARF ultrasound can be transmitted over a fraction of a millisecond to generate a localised transient tissue displacement on the order of a few tens of μm, i.e. the ARF-generated vibration pattern can comprise a non-zero displacement transient at the focal region and substantially no displacement elsewhere[14-17].

One possibility for ARF-LOVIT is to acquire one PA image prior to the ARF push (i.e. in the absence of displacement at the focus region), and a second image immediately after the push when the non-zero displacement transient at the focus region is present. A difference image then highlights the signal from optically absorbing structures located inside the displacement region. Direct clutter, in contrast, originates from outside the imaged region where no displacement occurs, and is thus eliminated. Echo clutter from acoustic scattering at echogenic structures inside the displacement region also shows up on the difference image, but at a different depth from where it was generated owing to the additional acoustic round-trip time as compared to PA signals. This allows spatial separation of echo clutter from true PA signal provided a narrow axial profile of the focused ARF beam.

Below we describe an example experimental study of one embodiment of ARF-LOVIT. In this example, a linear array of acoustic detectors is employed, where optical irradiation is provided by rows of fibre-optic illuminators that flank the linear array.

1. THEORY

ARF-LOVIT clutter reduction employs localised transient tissue displacement which is remotely induced inside the tissue by transmission of an ultrasonic focused beam (ARF beam). The high intensity ultrasound in the focus of the ARF beam generates a volumetric radiation force upon absorption and backscattering. Integration of this force over the duration of the transmission period (few 100 microseconds) results in an impulse transfer to the tissue (ARF push) that is able to initiate a localised tissue displacement of up to several tens of micrometres in magnitude, limited by the tissue elasticity and ultrasound safety standards. The theoretical considerations presented below assume that ARF beam transmission is implemented together with PA data acquisition using the same linear array transducer. This is a preferred mode of operation for clinical implementation of LOVIT because in such a setup the ARF beam is inherently aligned with imaging beamforming, and the ARF push position can be flexibly chosen via the transmit phase of the individual transducer elements. However, the theory can be readily adapted for different ARF beam configurations (or indeed for other approaches of generating vibration patterns which produce localised displacement transients) and different types of acoustic detectors, whether single element, two-dimensional arrays, ring arrays, or other configurations.

A first PA image is acquired prior to the ARF push, and a second one after the push. The ARF push in-between the two acquisitions leads to a spatially confined tissue displacement at the time of the second acquisition relative to the first acquisition. The spatial extent of the displacement region is determined both by the size of the ARF focus and by the shear wave propagation during the transmission period. It is assumed that this period is short enough so as to provide a narrow and short region of tissue displacement confined to the size of the ARF focus in all three directions. It is further assumed that: the ARF beam axis runs parallel to the transducer's axial direction, the ARF intensity is only a function of the coordinates of the imaging plane (x: lateral direction parallel to the linear array; z: axial direction), and the local displacement has only an axial component $\Delta z(x, z)$ (see FIG. 1). These assumptions simplify the theoretical analysis, and in practice can be relaxed (see the discussion section).

Firstly we consider a situation without clutter, where a single hypothetical point absorber is located at point (x, z) in the imaging plane and inside the displacement region. The pre-ARF PA image shows the point-spread function (PSF), centred at (x, z) (FIG. 1b, left side). The amplitude U is proportional to the local fluence and the absorption cross-section of the point target. The post-ARF PA image shows the same PSF but shifted by $\Delta z(x, z)$ in axial direction (FIG. 1b, right side). On subtracting the two images a new image is obtained, with a signal occurring at point (x, z) but with a different point-spread function (PSF') and a different amplitude (U') (FIG. 1c). U' and PSF' are determined by eq. 1:

$$u'(x, z) = U \cdot [PSF(x, z - \Delta z) - PSF(x, z)] \quad (1)$$
$$\equiv -U \cdot \Delta z \cdot \frac{d}{dz} PSF(x, z)$$
$$\doteq U' \cdot PSF'(x, z)$$

where $U' \doteq U \cdot \Delta z \frac{2\pi}{\lambda_0}$ $$PSF'(x, z) \doteq -\frac{\lambda_0}{2\pi} \frac{d}{dz} PSF(x, z)$$

To maintain sensible units and magnitudes for both U' and PSF', the acoustic wavelength at the centre frequency of the imaging probe, $\lambda_0$, was introduced. Assuming a simple cosine model for the axial profile of the PSF, the above definition ensures that PSF and PSF' have equal amplitude.

Eq. 1 illustrates that the PSF' of the difference image is in first approximation the axial derivative of the initial PSF, and the amplitude U' is proportional to both the initial amplitude U and the displacement $\Delta z$. The linear approximation to the axial derivative in eq. 1 holds for $\Delta z/\lambda_0 < 0.5$. This describes the reality well, where achievable displacements (on the order of few tens of micrometres) are far smaller than the wavelength typically used for imaging (e.g. 200 micrometres for a 7.5 MHz centre frequency probe).

Figure 2:
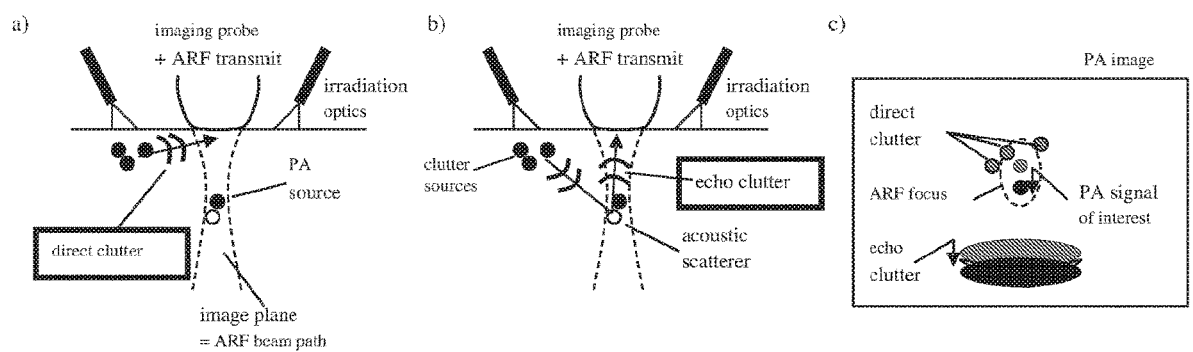
FIG. 2: *a*) Example origin of direct clutter. *b*) Example origin of echo clutter. *c*) PA signals of interest, direct clutter, and echo clutter are differently influenced by ARF-induced tissue displacement.

Next, clutter is taken into account. In this example, direct clutter emerges from optically absorbing structures that are located outside the imaging region, but directly exposed to the irradiating laser light (FIG. 2a). The resulting strong PA transients, even though detected by the probe at an angle where elevational sensitivity is low, obscure the weak PA signals from structures that are hidden deep inside the tissue. Echo clutter (FIG. 2b) may be generated by the same PA transients that cause direct clutter, but via acoustic scattering at echogenic structures located inside the imaging region. Epiphotoacoustic images of the human body usually show both clutter types, and it is impossible to distinguish clutter from "true" PA signal in a conventional image. This limits the effective imaging depth to typically less than one centimetre, even if a larger depth would be feasible given the optical penetration depth and the acoustic sensitivity. In general, clutter will tend to originate from any strong optical absorber that is not at the region being imaged, and it is more likely to arise at locations close to the site of optical irradiation where the optical fluence is greatest. In the example experimental study, a linear-array acoustic receiver is employed with lines of fibre-optic illuminators flanking the array. The most likely position of clutter sources is therefore outside the imaging plane of the array. For systems employing two-dimensional matrix arrays, ring arrays, or other acoustic transducer configurations, which may be used for volumetric PA imaging, this may not be true, and depending on the pattern of optical irradiation that is chosen, clutter sources may exist within the field of view of the receiver.

ARF-LOVIT theoretically allows full cancellation of both direct and echo clutter if ideal conditions are met. An ARF push that is in elevation confined to the imaging plane (as in the case where the same transducer is used for ARF and imaging) does not displace the PA clutter sources that lie outside the imaging plane (see FIG. 2c), and an ARF push that is spatial confined laterally and axially to an imaged region does not displace the PA clutter sources away from this region, thus direct clutter (i.e. the PA signal from these sources) does not show up in the LOVIT difference image. Echo clutter on the other hand is caused by acoustic scattering of the same PA transients from within the imaging plane. Because echogenic structures are displaced together with the tissue, echo clutter from scattering inside the displacement region cannot be eliminated. However, this echo clutter shows up at a different depth in the image to the PA signals, because the ultrasound that ultimately leads to echo clutter propagates through the tissue both from the source of clutter to the echogenic structure and from the echogenic structure to the acoustic receiver. Therefore, provided the axial extension of the ARF focus is small enough, direct PA signals and echo clutter are spatially separated (see FIG. 2c), and the LOVIT image shows PA signals from inside the displacement region free of both direct and echo clutter.

This section illustrates that the LOVIT image of the displacement region can be perceived as an original PA image but without clutter, compounded with the spatial distribution of the displacement Δz(x, z) and with a slightly changed PSF. The original PSF can again be obtained by spatial integration and the original amplitude by calibration for Δz. By scanning the imaging plane with the ARF focus, a clutter-free composite LOVIT image can thus be generated of the full imaging plane which conserves the true PA image, but eliminates clutter. The conservation of absolute signal amplitude by LOVIT is important in view of data analysis that relies on accurate amplitude, such as blood oxygen saturation imaging.

2. MATERIALS AND METHODS

A goal of the experimental study was the proof of principle of clutter elimination using ARF-LOVIT. In a preferred mode of implementation of ARF-LOVIT, the same transducer is used both for ARF beam transmission and for imaging. This is technically feasible, and already commercially implemented for radiation force elastography[14,15]. However, this study used a separate transducer for ARF beam transmission, in conjunction with a commercial ultrasound scanner for imaging.

2.1 Equipment and Setup

A commercial ultrasound scanner was used (Z.one® from Zonare Medical Systems Inc. USA) for PA imaging, in conjunction with a linear array probe (L10-5, Zonare). When operated in its research mode, the z.one facilitated parallel readout and storage of channel data from a subaperture of 64 elements out of the 128 element array. This allowed the acquisition of a PA frame with 19 mm aperture and several centimetres depth after each laser pulse, and storage of long frame sequences (up to minutes at the laser pulse repetition rate) on internal memory for subsequent read-out. The L10-5 featured a bandwidth (−3 dB) of 5 to 10 MHz and 7.5 MHz centre frequency corresponding to an acoustic wavelength of 200 μm. For PA signal generation, a Q-switched Nd:YAG laser (ELEN, Italy) was used at 1064 nm wavelength, delivering 70 mJ per pulse with a 7 ns pulse duration, at 10 Hz repetition rate. The laser light was guided via a bifurcated fibre-optic bundle (Fibreoptic, Switzerland) through two profile converters, both at the same side of the linear probe, generating a line of irradiation of 20 mm length and about 5 mm width parallel to one long side of the linear aperture.

Besides PA imaging, the z.one was used for additional purposes. First, it allowed the acquisition of conventional B-mode ultrasound images of the investigated phantoms for comparison of the PA images with "anatomical" features seen in B-mode. Second, pulse-echo channel data could be acquired at a high framerate of 2000 Hz for characterising the displacement magnitude in the ARF focus and the subsequent shear-wave propagation using correlation-based tracking of the axial phase. This was important in view of interpretation of the LOVIT results.

Figure 3:
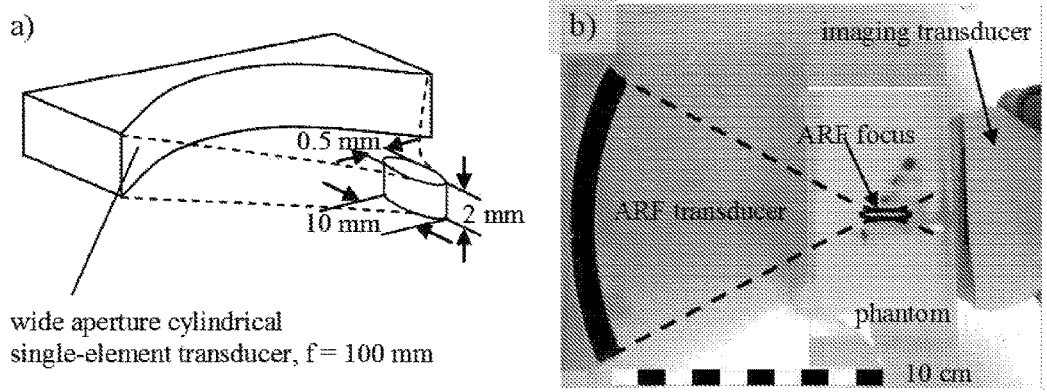
FIG. 3: *a*) Schematic view of the ARF transducer, showing dimensions of its focal region. *b*) Detail view of the experimental setup showing the ARF transducer and the imaging probe, together with a phantom.

For ARF beam transmission a separate cylindrically shaped single-element transducer was custom-designed to provide a flat beam with a narrow focus in the lateral dimension of the beam plane, but wide in the elevational dimension (FIG. 3a). This approximately mimicked the spatial characteristics of an ARF push that would have been produced if the linear array probe had been used to generate it. This ARF transducer could be scanned in a plane using two remote-controlled motorised linear stages (T-LLS105, Zaber), and the imaging array was aligned opposite to the ARF transducer, such that the imaging plane matched the ARF-beam scanning plane. FIG. 4b shows a detail view of the setup with the ARF transducer and the imaging transducer inside a water tank. The size and location of the phantom is also illustrated and the focal position inside the phantom is indicated. The ARF transducer was driven at its centre frequency (2 MHz) using a waveform generator (33220A, Agilent) via an RF-amplifier (Tomco).

2.2 Tissue Phantom

Figure 4:
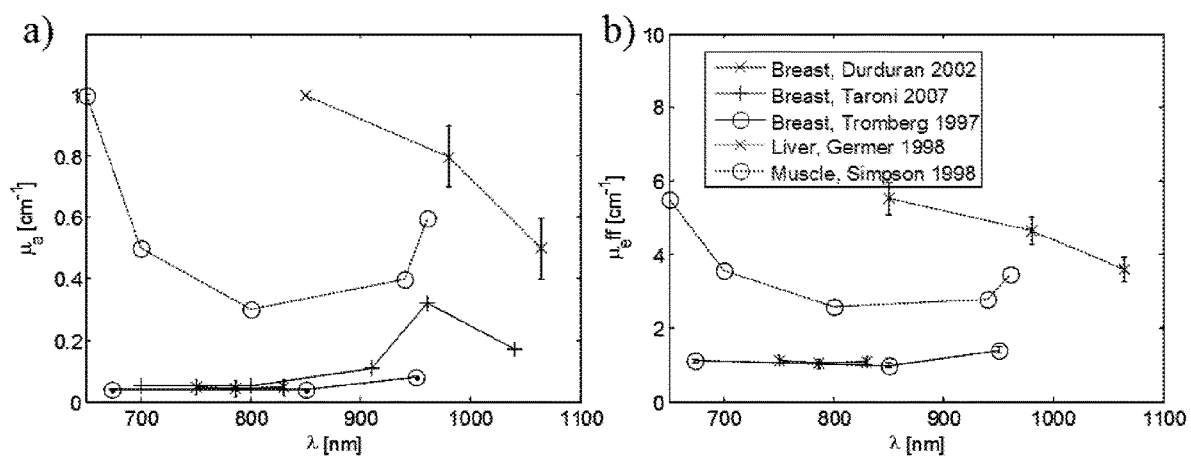
FIG. 4: Tissue optical properties for human breast, liver, and skeletal muscle. *a*) Absorption coefficient. *b*) Effective attenuation coefficient.

The tissue phantoms were intended to mimic average optical properties of human tissue in the NIR range where PA imaging can in theory achieve several centimetres imaging depth. FIG. 4 summarises optical properties of various human tissue types in the range from 650 nm to 1100 nm, quoted from [18-20] [21] [22] [23]. The effective optical attenuation coefficient of the bulk tissue determines the depth-dependent PA signal level whereas the bulk absorption coefficient determines the level of direct clutter, and together with the tissue echogenicity the echo clutter level. Therefore optical attenuation, absorption and acoustic echogenicity together determine the clutter-limited imaging depth. In addition to that, the phantom had to have an elasticity similar to that of tissue.

In order to meet all these criteria the phantoms were built from gelatine for elasticity (Fluka analytical, from porcine skin), $TiO_2$ for optical scattering (Sigma Aldrich), India ink for optical absorption (951 black Winsor & Newton), and cellulose for echogenicity (Sigmacell Type 20). For the assessment of the effect of LOVIT on contrast and imaging depth, 2-mm-diameter gelatine cylinders that were optically absorbing (India ink) and hypoechoic (no cellulose) were embedded in the phantom, imitating blood vessels whose true position could be identified on B-mode US.

Three different phantoms were built with slightly differing optical properties. The compositions of the phantoms (all % in weight), as well as key optical properties, are listed in Table 1. The absorption coefficient of the inclusions was estimated based on a priori photometric measurement of the India ink. The absorption in the "skin" layer of phantom III was estimated based on the absorption coefficient and the thickness of the layer. The bulk effective optical attenuation coefficient $\mu_{eff}$ at the wavelength used for the experiments (1064 nm) was determined a posteriori based on the depth dependent amplitude of the PA signal of the absorbing inclusions, and results match the $\mu_{eff}$, in the wavelength range between 650 to 950 nm of tissue between breast and muscle. The bulk absorption coefficient was probably equal to water, with cellulose having no influence (see results section). Cellulose is a popular agent for acoustic scattering in ultrasound phantoms, with concentrations ranging from 0.25%[24] to several percents[25]. We chose an intermediate concentration.

TABLE 1

Composition and key optical properties of the phantoms

|  | Gelatine | $TiO_2$ | India ink | Cellulose | $\mu_{eff}$ | $\mu_{eff}$ |
|---|---|---|---|---|---|---|
| Inclusions | 5% | 2‰ | 0.84‰ | — |  | 5 cm$^{-1}$ ± 0.1 cm$^{-1}$ (ink) |
| Phantom I | 5% | 2‰ | — | 2% | 1.8 cm$^{-1}$ ± 0.2 cm$^{-1}$ | 0.17 cm$^{-1}$ ($H_2O$) 0 (cellulose) |

TABLE 1-continued

Composition and key optical properties of the phantoms

| | Gelatine | TiO$_2$ | India ink | Cellulose | $\mu_{eff}$ | $\mu_{eff}$ |
|---|---|---|---|---|---|---|
| Phantom II | 5% | — | — | 2% | 1.2 cm$^{-1}$ ± 0.2 cm$^{-1}$ | 0.17 cm$^{-1}$ (H$_2$O) 0 (cellulose) |
| Phantom III | =phantom II, but with a thin layer of inclusion mixture added on top to mimic optical absorption in the skin. | | | | The absorption in the thin layer was estimated to 30%, based on the absorption coefficient (5 cm$^{-1}$) and the thickness of the layer. | |

2.3 ARF-LOVIT Acquisition Procedure

The first experimental step was the characterisation of the magnitude and spatial extent of the ARF-induced localised displacement and of the subsequent shear wave propagation. For this purpose the z.one was operated in the research mode for acquisition of pulse-echo RF channel data. An internal trigger of the z.one triggered the acquisition of a sequence of 30 pulse-echo frames at 2000 fps frame rate (total 15 ms duration). One ms after the first frame, an ARF beam was transmitted for 0.5 ms duration. After ARF beam transmission, the time-dependent local displacement inside the phantom could be observed in the reconstructed pulse-echo RF frames. Pulse-echo frames were reconstructed offline using a frequency-domain synthetic aperture algorithm[26, 27]. The local displacement was determined using correlation-based axial tracking of the RF echo phase[28] resulting in a movie of the local displacement after the ARF push and of the subsequent shear wave propagation. Both the magnitude of the displacement and the shear wave speed could be determined from this movie.

For the ARF-LOVIT experiment, the z.one was operated in the research mode for RF channel data acquisition, but with ultrasound transmission inactive and with the laser active. The z.one triggered the acquisition of a sequence of 20 PA reference frames (without preceding ARF push) and 10 PA post-ARF frames. In addition, 20 frames with only noise (without laser irradiation) were acquired to characterise the stochastic noise level. A single conventional PA image was obtained from averaging the 20 reference frames with laser irradiation. A pre-ARF image and a post-ARF image were obtained by averaging 10 reference frames and the 10 post-ARF frames, respectively, and a single LOVIT image was obtained taking the difference of the two images, multiplied by a factor of 0.5 so that the conventional PA image and the LOVIT image were obtained from the same number of acquisitions and exhibited the same stochastic noise level.

This procedure provided a LOVIT image from inside the spatially confined displacement region around a single ARF focus position. In order to obtain a large field of view, the imaging plane was scanned with the ARF focus in steps of 2 mm laterally and 5 mm axially, and a separate LOVIT image was recorded for each focal position. Then a composite LOVIT image was generated by mosaicking from all focus positions.

2.4 Data Display

The field of view (FOV) of the reconstructed frames was 19 mm (lateral) by 50 mm (axial) for the fast pulse-echo mode frames, and 38 mm (lateral) by 50 mm (axial) for the PA images. The lateral extent of the FOV for the PA images was deliberately chosen larger than the extent of the receiving aperture (19 mm) for two reasons. First, this allowed simpler comparison of the PA images with the z.one's conventional pulse-echo images. Second, this accounted for the possibility of receive angles pointing outside the axial projection of the active aperture. For display, B-mode PA images were obtained using envelope detection and logarithmic compression. All displayed B-mode PA images cover the same amplitude range, starting at an identical level and spanning 40 dB, for fair comparison of all the results.

3. RESULTS 3.1 Conventional Combined PA and Pulse-Echo Imaging

Figure 5:
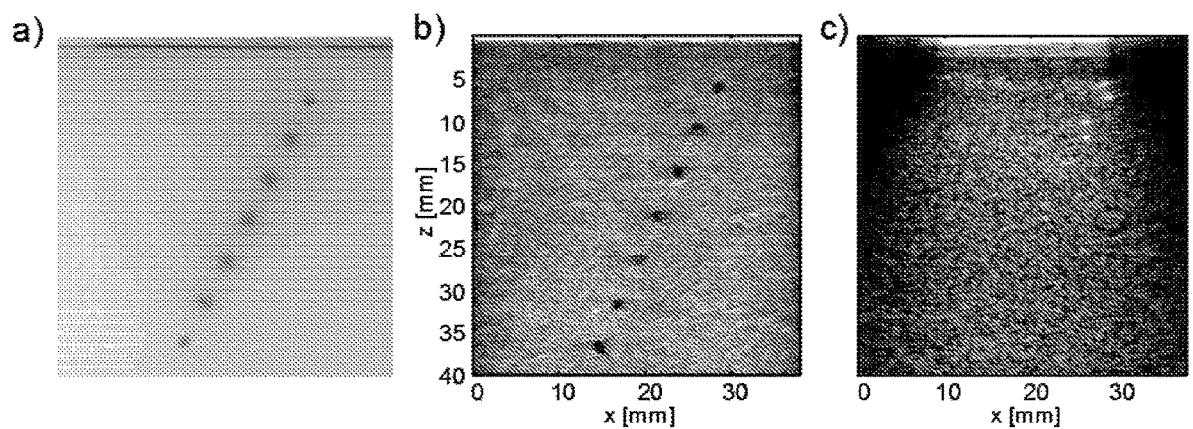
FIG. 5: *a*) Photograph of a section through phantom III at the location of the imaging plane, taken after the experiment. *b*) B-mode ultrasound of the phantom. *c*) Photoacoustic B-mode image.

FIG. 5a shows a photograph of a section through phantom III, where the imaging plane was located for subsequent experiments. The imaging plane was aligned perpendicular to the cylindrical inclusions, and the cross-sections of the inclusions can be seen as circular grey areas arranged along an oblique line. FIG. 5b is the z.one B-mode ultrasound image obtained at the same position, which allows the identification of the optically absorbing inclusions as hypoechoic regions inside the echogenic background. FIG. 5c is the conventional PA B-mode image. This image represents the state-of-the-art of epiphotoacoustic imaging without clutter reduction. In FIG. 5c, only the most superficial two inclusions can be clearly identified on the PA image. The reason for this is clutter, which obscures the deeper inclusions and limits imaging to depths far less than those which could be achieved if optical attenuation and transducer noise were the only limiting factors. A goal of the present study was the demonstration of both improved contrast and imaging depth using LOVIT, as compared to this conventional image.

3.2 Shear Wave and Displacement Characterisation

Figure 6:
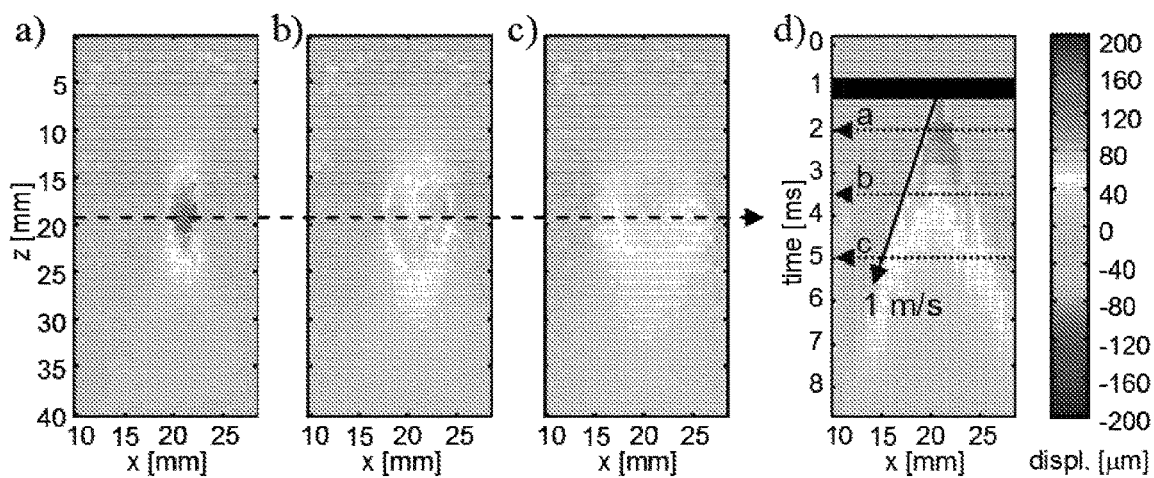
FIG. 6: *a*) to *c*) Snapshots of shear wave propagation after the ARF push at different points of time and *d*) local displacement as function of time at constant depth indicated by the dashed horizontal line in (*a*) to (*c*). The times at which the snapshots were taken are indicated in (*d*) by dotted horizontal lines. The ARF beam transmission period is indicated with a black bar, and the slope of the shear wave propagation with a solid arrow.

The magnitude of the ARF-induced localised displacement as well as the spatial extension of the displacement region are important parameters for the performance of ARF-LOVIT. For assessment of these parameters the ARF focus was centred in the FOV, and a fast pulse-echo sequence was acquired and analysed as described in the previous section. FIG. 6 displays a sequence of displacement snapshots taken at different times after the ARF push, as well as the displacement along a constant depth as function of time. The time evolution shows the localised displacement immediately after the end of the ARF push as well as the subsequent generation and propagation of transient shear waves. Note that all displacements are positive, although the ARF push acted in the negative axial direction towards the imaging probe. This is a mere convention. The temporal slope of the shear wave propagation allowed the determination of the shear wave speed to 1 m/s±0.1 m/s. Based on the time evolution of the displacement, the post-ARF acquisition delay was chosen to be 1 ms for the subsequent LOVIT experiment. The achieved displacement magnitude was 130 μm, and the size of the displacement region was roughly 2 mm (laterally) by 5 mm (axially). This also determined the scanning stepsize for the generation of the large FOV composite LOVIT image.

3.3 ARF-LOVIT, Single Push Location

Figure 7:
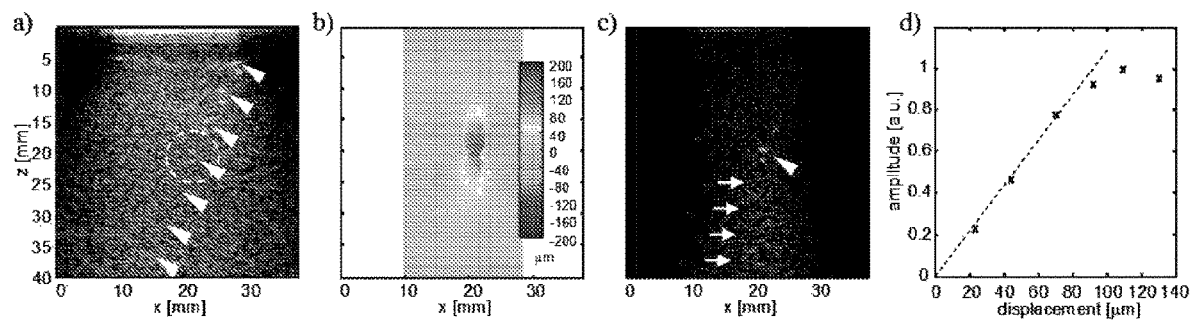
FIG. 7: *a*) Conventional PA image. *b*) Localised displacement after ARF push. *c*) Resulting LOVIT image. *d*) Dependence of LOVIT amplitude on displacement.

In a second experimental stage, LOVIT clutter reduction was demonstrated with a single ARF focus position. FIG. 7a is the conventional PA image of phantom III, with the inclusion positions indicated by white arrowheads. As previously mentioned, only the most superficial two inclusions can be clearly identified. The dashed circle indicates where the ARF focus was positioned for LOVIT clutter reduction, and FIG. 7b shows the localised displacement 1 ms after the ARF push, the time of post-ARF acquisition in this experiment.

The resulting LOVIT difference image, FIG. 7c, shows strongly improved contrast compared to the conventional image, leading to the visibility of the inclusion inside the displacement region (indicated by white arrowhead). Posterior to the ARF focus position, the difference image shows a region of diffuse signal (left boundary indicated by small white arrows) which extends down to the bottom of the image. This is presumably echo clutter, which emerges from acoustic backscattering inside the displacement region but turns up in the difference image at a larger depth owing to the longer acoustic round-trip time. The PA transients that result in echo clutter originate from distributed sources and thus give the echo clutter region a large spatial extension.

FIG. 7d shows the amplitude of the PA signal in the difference image (LOVIT amplitude) as a function of the localised displacement magnitude. For this measurement the ARF beam transmission period was changed from short to long, to generate different displacement magnitudes. The result confirms the linear relation between displacement and LOVIT amplitude which was suggested in eq. 1, for displacements smaller than 60 µm. The LOVIT amplitude achieves a maximum at around 100 µm displacement corresponding to half the acoustic wavelength at the imaging centre frequency, and then decreases again. At the maximum LOVIT amplitude, the same SNR is obtained as would be achieved with simple averaging over the identical number of frames, but with clutter virtually eliminated around the absorbing inclusion.

3.4 ARF-LOVIT, 2D Scan

Figure 8:
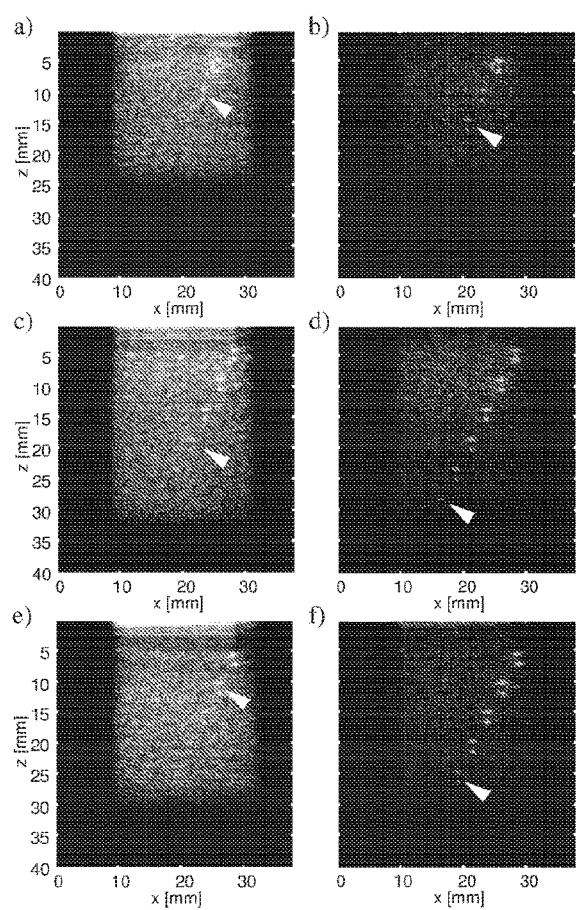
FIG. 8: Composite LOVIT results (*b*, *d*, *f*) of the three phantoms, compared to the conventional PA images (*a*, *c*, *e*). *a*) and *b*) Phantom I. *c*) and *d*) Phantom II. *e*) and *f*) Phantom III.

The LOVIT result from a single ARF focus position demonstrated that, within the localised displacement region, clutter can be largely eliminated and thus contrast of true PA signals strongly improved. To demonstrate a process for achieving a full-FOV clutter free image, the phantom was therefore 2-dimensionally scanned with the ARF focus, in steps of 2 mm laterally and 5 mm axially. A composite LOVIT image was then generated by mosaicking as explained in the materials and methods section. The results for the different phantoms are shown in the second column of FIG. 8. For a fair comparison, the same mosaicking procedure as for the LOVIT composite image was employed to generate the conventional PA images. These results are shown in the first column of FIG. 8.

All three examples demonstrate both improved contrast and increased imaging depth when using LOVIT compared to conventional PA imaging. The residual background signal of the LOVIT image is a combination of system noise, residual echo clutter (see discussion), and true inhomogeneous optical absorption in the imaging plane. Limited by this residual background, the deepest visible inclusion that can unambiguously be identified is indicated for each image in FIG. 8 (white arrowhead). The imaging depth obtained with LOVIT, as well as the clutter-limited conventional imaging depth, is listed in Table 2 for the different phantoms. The theoretical imaging depth limited by only system noise is also listed, extrapolated based on the slope of the depth-dependent PA amplitude and on the residual noise level. An SNR of 10 dB was assumed as threshold for inclusion detection, in agreement with the detection threshold found in the conventional PA images.

TABLE 2

Imaging depth obtained with the different phantoms and the different methods

| | conventional PA imaging depth | LOVIT | noise-limited imaging depth | increase in imaging depth |
|---|---|---|---|---|
| Phantom I | 10-15 mm | 15-20 mm | 22 mm | 5 mm |
| Phantom II | 15-20 mm | >30 mm | 30 mm | 10-15 mm |
| Phantom III | 10-15 mm | >25 mm | 30 mm | 15-20 mm |

3.5 Optical Properties Assessment

The effective optical attenuation coefficient of the different phantoms was estimated a posteriori from the slope of the depth-dependent PA amplitude of the inclusions. This slope was 1.7 cm$^{-1}$, 1.5 cm$^{-1}$, and 1.35 cm$^{-1}$ for phantoms I, II, and III, respectively. The standard error was around 0.1 cm$^{-1}$. Assuming homogeneous irradiation of the phantom surface and a Beer-Lambert law this translates directly into the effective optical attenuation coefficient $\mu_{eff}$. However irradiation was not homogeneous but occurred on a single line adjacent to the linear probe. Based on the diffusion approximation solution for a line source[28a], a 0.2 cm$^{-1}$ lower $\mu_{eff}$ is more realistic. For phantom I, only amplitude measurements close to the surface were available, which might have lead to an underestimation of $\mu_{eff}$ owing to the boundary conditions. Earlier phantom experiments with the same concentration of TiO$_2$ as in phantom I, but 0.5% instead of 2% cellulose, suggested a $\mu_{eff}$ of 1.8 cm$^{-1}$ when deeper amplitude measurements were available owing to lower echo clutter. In summary the $\mu_{eff}$ of phantom I was larger than 1.5 cm$^{-1}$, but potentially around 1.8 cm$^{-1}$±0.2 cm$^{-1}$, and $\mu_{eff}$ of phantom II and III was 1.2 cm$^{-1}$±0.1 cm$^{-1}$.

The bulk absorption coefficient pa was then calculated as follows. The reduced scattering coefficient of the 0.02% TiO$_2$ was estimated to 2.6 cm$^{-1}$ 1/g or 5.2 cm$^{-1}$ [29]. Assuming a simplified relation $\mu_{eff}^2 = 3\mu_a \cdot \mu_s^1$, and based on the ratio of the pen obtained with and without TiO$_2$, the reduced scattering coefficient of the cellulose alone was 4.2 cm$^{-1}$±2.4 cm$^{-1}$. In a next step the bulk $\mu_a$ (combination of water and cellulose) could be calculated to 0.12 cm$^{-1}$±0.06 cm$^{-1}$. The $\mu_a$ of the water alone at 1064 nm is 0.15 cm$^{-1}$ [30]. Therefore we assumed that the bulk $\mu_a$ was determined by the water alone, i.e. the contribution of the cellulose was negligible.

4. DISCUSSION

The results demonstrate that ARF-LOVIT facilitates strongly improved contrast and imaging depth in a situation where PA contrast is limited by clutter rather than by system noise. With various phantoms mimicking optical properties in the range between human breast and muscle tissue, imaging depth could be increased close to the noise limit, suggesting that close to full clutter elimination would be possible with ARF-LOVIT. The largest increase in imaging depth was obtained with phantom III, from 10-15 mm to 30 mm, more than doubling the conventional imaging depth. The smaller conventional imaging depth in phantom III as compared to phantom II is explained with the higher echo clutter level owing to the absorbing "skin" layer. Comparison of the phantom II and III results demonstrates that the same noise-limited imaging depth can be achieved using LOVIT, independent of the initial clutter level.

Optical absorption in the skin layer has previously been shown to be a prominent source of echo clutter which significantly limits imaging depth in clinical epiphotoacoustic imaging of the breast[31]. This may be especially important for patients with high melanin content, who may be excluded from PA imaging if no clutter reduction method is used. Previously DCA was developed for clutter reduction. DCA however allows only partial clutter reduction by typically a factor of 3, corresponding to an increase by 7 mm in imaging depth when assuming a $\mu_{eff}$ of 1.5 cm−1. In comparison, our results demonstrate that LOVIT should allow full clutter elimination and thus noise-limited imaging, which in the case of phantom III led to an increase in imaging depth by 15 to 20 mm. LOVIT can therefore make a significant contribution to successful clinical epiphotoacoustic imaging.

Figure 9:
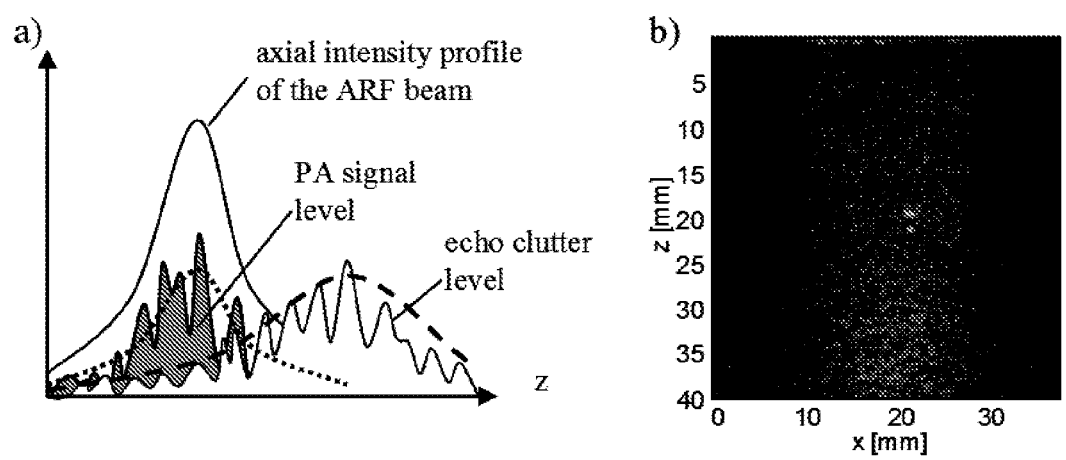
FIG. 9: *a*) Sketch for the overlap of PA signal and residual echo clutter in the LOVIT image. *b*) Difference image of two post-ARF PA frames with adjacent ARF focus positions.

Two factors contributed to the excellent performance of LOVIT in the presented proof-of-principle study. First, a fairly large localised displacement, in the range of half the acoustic imaging wavelength, allowed maximum LOVIT amplitude. Second, and more important, a small displacement region allowed the substantial elimination of echo clutter. For full elimination of direct clutter using LOVIT tagging of true PA signal, tissue displacement should be confined to a tightly bounded region. This condition was met because ARF beam transmission was strongly focused and of short duration, and the tagged image was acquired before the shear wave generated by the ARF beam had spread too far. Echo clutter elimination on the other hand typically requires a displacement region that is particularly well-confined in the axial direction, to allow spatial separation of true PA signal and echo clutter that both originate from the same region. Generally, this requirement cannot be fully satisfied because significant displacement is generated all along the ARF beam path even with a focused beam, leading to an overlap of PA signals and echo clutter in the difference image. This is illustrated in FIG. 9. LOVIT amplifies PA signals proportional to the displacement Δz(x, z) determined by the ARF beam profile. At the same time, it amplifies echo clutter at larger depth, approximately proportional to a stretched profile, related to but not necessarily equal to z(x, z/2), due to the extended round-trip time of the echoes relative to direct PA signal. Because Δz(x, z) is not perfectly confined in the axial direction, the two profiles overlap resulting in residual echo clutter in the LOVIT image at point (x, z). For this reason the axial length of the displacement region should generally be kept as short as possible. This was achieved in the present study by a small ARF depth-of-focus (well-confined in the axial direction) on one hand and, on the other, by taking advantage of the slow shear wave propagation (as possessed by tissue) during ARF beam transmission and during the post-ARF acquisition delay.

For further reduction of echo clutter, advantage may be taken of the possibility to vibration tag the signals using a strong ARF focus at one depth, which will vibrate the acoustic scatterers at that depth, and then inspect the signals at the (e.g. double) depth expected for the corresponding echo clutter, to detect whether the vibration coding is present and, if it is, eliminate these signals from the final image. Advantage may also be taken of the opportunity to subdivide a very large ARF focusing aperture into different sub-apertures, so as to create different ARF beams where each will steer the ARF-generated displacement vector in a different direction. This technique can direction-code, as well as vibration-code, the clutter signal, for subsequent recognition and elimination. These methods may be applied alone or in combination.

In clinical practice, both a large displacement and a tightly confined displacement region can be problematic and are partially exclusive. Displacement magnitudes that are typically obtained in human tissue with radiation force elastography are situated in the range of 5 to 40 μm, obtained with ARF beam transmission periods between 100 and 500 μs[14-17]. The maximum mechanical index (MI) limits the acoustic peak intensity of the ARF beam, thus larger displacements can only be achieved with a longer ARF beam transmission period. Because shear wave propagation already occurs during ARF beam transmission, a longer period above a certain threshold comes with a larger displacement region which in turn reduces the capability of echo clutter cancellation.

For the above reasons, in the case where echo clutter prevails over direct clutter, a tightly confined displacement region with moderate displacement magnitude (e.g. around 20 μm) might be preferable compared to a larger but less localised displacement. In this respect the achievable SNR of this first example of ARF-LOVIT ($SNR_{lovit}$) (i.e. without implementing additional coding schemes as mentioned in the paragraph above) compared to conventional PA imaging assuming no clutter and averaged over the same number of acquisitions ($SNR_{conv}$) is of interest (SNR gain G). Eq. 1 yields a useful relation between the displacement and G for this simple situation:

$$\Rightarrow G \doteq \frac{SNR_{lovit}}{SNR_{conv}} = \frac{U'/\sqrt{2}}{2U/\sqrt{2}} = \frac{U \cdot \Delta z \cdot 2\pi/\lambda_0}{2U} = \frac{\Delta z \cdot \pi}{\lambda_0} \quad (2)$$

For Δz=20 μm and $\lambda_0$=200 μm, the SNR gain becomes G=π/10. This means that with this first example implementation of LOVIT and with displacements typical for radiation force elastography, the SNR of the PA image is reduced by a factor of three by ARF-LOVIT compared to simply averaging. In alternative implementations of ARF-LOVIT advantage may be taken to increase the SNR by increasing the signal for large displacement magnitudes by, for example, processing the acoustic signal envelope rather that the RF signal, or by the use of signal amplitude "unwrapping" by obtaining multiple results either as a function of displacement magnitude or as a function of acoustic receiver wavelength. The alternative techniques discussed above for calculating the final image, i.e. other than difference imaging, may also help to further improve the final SNR.

A preference for a short displacement region (i.e. one that is well confined in the axial direction), for successful echo clutter reduction, sets a limitation to the real-time capability of LOVIT: a short displacement region goes hand in hand with a large number of ARF focus positions for a full FOV composite LOVIT image. With a focal size of the displacement region of 2 mm laterally and 5 mm axially, the minimum amount of acquisitions required to cover a FOV of 20 mm by 40 mm is 80 post-ARF frames plus one reference frame in minimum. If motion artifacts are to be avoided, 80 reference frames, acquired directly before the ARF push, are preferable. This would result in 160 acquisitions, or 16 seconds acquisition time for a single composite image. Alternatively, lasers with a higher pulse repetition rate might be used to increase acquisition speed. However, higher pulse repetition rates are only possible with reduced pulse energy in order to comply with the tissue's maximum permissible laser exposure[32]. This leads to further reduced enhancement of SNR of LOVIT over that for conventional PA imaging.

On the other hand, the total number of acquisitions for a single composite image, and thus acquisition time, can be reduced by employing more sophisticated acquisition and data processing schemes than the one used for this proof-of-principle study. In a first step the number of acquisitions can be reduced by a factor of two because the pre-ARF reference frames are obsolete. Post-ARF frames obtained with spatially separate focal zones can serve as respective reference frames. FIG. 9b shows the result of this approach for phantom III, for two focal zones adjacent to each other, around the position of the absorbing inclusion already shown in FIG. 7c. The same contrast improvement as in FIG. 7c is obtained!

A high acquisition rate might ultimately conflict with ultrasound safety because the rate of ARF beam transmissions is limited by the maximum permissible average ultrasound intensity. If this is the case, the total number of ARF beam transmissions can potentially be reduced by taking advantage of shear wave propagation, and acquiring multiple PA frames after a single ARF push. With multiple focal positions during a single push, the initial displacement distribution can be tailored in a way that leads to directive shear wave propagation, a method similar to what is called "supersonic shear imaging" of shear-wave speed in ARF shear wave elastography[15]. Such directive propagation requires an elongated shear wave-front, in conflict with the narrow displacement region earlier required for efficient echo clutter elimination. However, at the crossing point of various such directed shear wave fronts, propagating at different angles, a narrow displacement region can be obtained by data processing. Furthermore, such shear waves, used with laser irradiation pulsed to produce the PA image at the appropriate time, may provide a convenient means of vibration tagging the clutter signals at their source, which is an alternative to vibration tagging of the true PA signals. In the present example experiment, these clutter sources were outside the imaging plane and would thus have required a separate ARF transducer to displace them, which would be inconvenient in a future system. The use of shear waves can overcome such inconvenience.

In a clinical application of LOVIT, cardiovascular, respiratory or other tissue motion can potentially influence and degrade the outcome of clutter reduction. However, LOVIT using ARF or shear waves is still possible provided that the time delay between pre- and post-ARF image frames is short enough such that tissue motion between the two frames is sufficiently small. If this is not possible then the effect of tissue motion on LOVIT performance may be removed by motion compensation prior to subtracting the tagged and the reference images. For example, a number of pulse-echo image acquisitions that occur shortly before each pre-ARF frame can be used for motion tracking, and tissue motion can be extrapolated from many such pulse-echo frames to the time of the post-ARF acquisition. Conversely, if the tissue motion is sufficiently localised and dynamic, as may be the case for small pulsating arteries or for shear waves produced by cardiac and/or vascular pulsations, it may represent an alternative means of inducing the displacement for implementing a passive form of LOVIT, i.e. without actively creating a localised vibration.

In summary, for this first example implementation of LOVIT, in the case where the ratio of the clutter level to the system noise is much larger than the SNR reduction with LOVIT, reduction in SNR is acceptable given the benefit of clutter elimination. However, the above discussed limitations to real-time capability count only for echo-clutter. Direct clutter can always be eliminated owing to the ability to narrowly localise the ARF beam in the lateral and elevation directions, even with a long ARF beam depth-of-focus. The benefits of this implementation of LOVIT therefore are: full direct clutter cancellation and partial echo clutter cancellation, and thus improved imaging depth over DCA; applicability to non-palpable tissue; and no special skills required. Further improvements in performance may be brought about by implementing extensions of the technique such as those described above (e.g. direction coding of the induced displacements for echo clutter cancellation and displacement amplitude phase-unwrapping, envelope processing, etc., for SNR improvement).

In addition to photoacoustic imaging, LOVIT has potential for clutter reduction in echo ultrasound, optical coherence tomography and other imaging techniques. In conventional US echography, where the acoustic signals are generated by acoustical irradiation of the body rather than optical irradiation, acoustic clutter may, for example, arise from acoustic scatterers outside the imaged region, which may generate clutter echoes that return to the acoustic receiver either directly (US direct clutter) or after being scattered by other echogenic structures (US echo clutter). Localised vibration tagging as described in the present invention can be used to reduce such US clutter, although the vibration should be generated in a sufficiently localised manner, bearing in mind that for ARF-LOVIT the clutter sources in a US image are acoustic scatterers and may therefore also affect the ARF beam. The use of shear wave or other sources of localised vibration can also be used to overcome such a potential problem. In OCT the strong and multiple optical scattering by tissue may generate substantial optical clutter. In the most common form of OCT, this is substantially reduced by the use of a highly collimated beam of light. However, not only does this not fully remove the possibility of optical clutter generation at depths where the beam has been diffused by scattering, it has the substantial disadvantage that to produce an OCT image this beam must be scanned, reducing image frame rate. Alternative parallel acquisition methods using large area detectors offer potential for high frame and volume rate imaging but suffer from poor, optical clutter-limited, image contrast. The LOVIT approach of the present invention can be used to reduce optical clutter in OCT and other optical imaging methods, such as diffuse optical tomography and optical computed tomography.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

[1] M. Xu and L. V. Wang, "Photoacoustic imaging in biomedicine", Rev. Sci. Instrum. 77(4), 41101-1-22 (2006)

[2] S. Hu and L. V. Wang, "Photoacoustic imaging and characterization of the microvasculature", J. Biomed. Opt. 15(1), 011101-1-15 (2010)

[3] H. F. Zhang, K. Maslov, G. Stoica and L. H. V. Wang, "Functional photoacoustic microscopy for high-resolution and noninvasive in vivo imaging", *nature biotech.* 24(7), 848-851 (2006)

[4] S. A. Ermilov, T. Khamapirad, A. Conjusteau, M. H. Leonard, R. Lacewell, K. Mehta, T. Miller and A. A. Oraevsky, "Laser optoacoustic imaging system for detection of breast cancer", 14(2), 024007-1-14 (2009)

[5] D. R. Bauer, R. Olafsson, L. G. Montilla and R. S. Witte, "3-D photoacoustic and pulse echo imaging of prostate tumor progression in the mouse window chamber", *J. Biomed. Opt.* 16(2), (2011)

[6] Y. Junjie, K. I. Maslov, Z. Yu, X. Younan and L. V. Wang, "Label-free oxygen-metabolic photoacoustic microscopy in vivo", *J. Biomed. Opt.* 16(7), 076003 (2011)

[7] B. Wang, E. Yantsen, T. Larson, A. B. Karpiouk, S. Sethuraman, J. L. Su, K. Sokolov and S. Y. Emelianov, "Plasmonic Intravascular Photoacoustic Imaging for Detection of Macrophages in Atherosclerotic Plaques", 9(6), 2212-2217 (2009)

[8] Y. Wang, X. Xie, X. Wang, G. Ku, K. L. Gill, D. P. O'Neal, G. Stoica and L. V. Wang, "Photoacoustic tomography of a nanoshell contrast agent in the in vivo rat brain", *Nano Lett.* 4(9), 1689-1692 (2004)

[9] T. D. Khokhlova, I. M. Pelivanov, V. V. Kozhushko, A. N. Zharinov, V. S. Solomatin and A. A. Karabutov, "Optoacoustic imaging of absorbing objects in a turbid medium: ultimate sensitivity and application to breast cancer diagnostics", *Appl. Opt.* 46(2), 262-272 (2007)

[10] M. Frenz and M. Jaeger, "Optimization of tissue irradiation in optoacoustic imaging using a linear transducer theory and experiments", *Photons Plus Ultrasound: Imaging and Sensing, Proc SPIE* 6856, 68561Y-1-13 (2008)

[11] M. Jaeger, L Siegenthaler, M. Kitz and M. Frenz, "Reduction of background in optoacoustic image sequences obtained under tissue deformation", 14(5), 054011-1-10 (2009)

[12] M. Jaeger, S. Preisser, M. Kitz, D. Ferrara, S. Senegas, D. Schweizer and M. Frenz, "Improved contrast deep optoacoustic imaging using displacement-compensated averaging: breast tumour phantom studies", 56(18), 5889-5901 (2011)

[13] M. Jaeger, D. Birtill, A. Gertsch, E. O'Flynn and J. Bamber, "Deformation compensated averaging for clutter reduction in epiphotoacoustic imaging in vivo", *J. Biomed. Opt.* 17(066007-1-8 (2012)

[13b] Lediju M A, Pihl M J, Dahl J J, Trahey G E. Quantitative assessment of the magnitude, impact and spatial extent of ultrasonic clutter. Ultrason Imaging. 30(3):151-68 (2008).

[13c] Lediju M A, Pihl M J, Hsu S J, Dahl J J, Gallippi C M, Trahey G E. A motion-based approach to abdominal clutter reduction. IEEE Trans Ultrason Ferroelectr Freq Control. 56(11):2437-49 (2009).

[13d] Podoleanu A G. Optical coherence tomography. J Microsc. Jun 18. doi: 10.1111/j.1365-2818.2012.03619.x. (2012)

[13e] Sandrin L, Tanter M, Gennisson J L, Catheline S, Fink M. Shear elasticity probe for soft tissues with 1-D transient elastography. IEEE Trans Ultrason Ferroelectr Freq Control. 49:436-46 (2002).

[13f] Gennisson J L, Muller M, Deffieux T, Tanter M, Fink M. Quantitative Viscoelasticity Mapping of Human Liver Using Supersonic Shear Imaging: Preliminary in Vivo Feasability Study. Ultrasound in Medicine and Biology. 35:219-29 (2009).

[14] K. Nightingale, M. S. Soo, R. Nightingale and G. Trahey, "Acoustic radiation force impulse imaging: In vivo demonstration of clinical feasibility", *Ult Med Biol* 28(2), 227-235 (2002)

[15] J. Bercoff, M. Tanter and M. Fink, "Supersonic shear imaging: A new technique for soft tissue elasticity mapping", *IEEE Trans Ult Ferr Freq Cont* 51(4), 396-409 (2004)

[16] D. Melodelima, J. C. Bamber, F. A. Duck, J. A. Shipley and L. Xu, "Elastography for breast cancer diagnosis using radiation force: System development and performance evaluation", *Ult Med Biol* 32(3), 387-396 (2006)

[17] D. Melodelima, J. C. Bamber, F. A. Duck and J. A. Shipley, "Transient elastography using impulsive ultrasound radiation force: A preliminary comparison with surface palpation elastography", *Ult Med Biol* 33(6), 959-969 (2007)

[18] T. Durduran, R. Choe, J. P. Culver, L. Zubkov, M. J. Holboke, J. Giammarco, B. Chance and A. G. Yodh, "Bulk optical properties of healthy female breast tissue", *Phys Med Biol* 47(2847-2861 (2002)

[19] N. Shah, A. Cerussi, C. Eker, J. Espinoza, J. Butler, J. Fishkin, R. Hornung and B. Tromberg, "Noninvasive functional optical spectroscopy of human breast tissue", *PNAS* 98(8), 4420-4425 (2001)

[20] P. Taroni, D. Comelli, A. Pifferi, A. Torricelli and R. Cubeddu, "Absorption of collagen: effects on the estimate of breast composition and related diagnostic implications", *J Biomed Opt* 12(1), 014021-1-4 (2007)

[21] B. J. Tromberg, O. Coquoz, J. B. Fishkin, T. Pham, E. R. Anderson, J. Butler, M. Cahn, J. D. Gross, V. Venugopalan and D. Pham, "Non-invasive measurement of breast tissue optical properties using frequency-domain photon migration", *Phil Trans R Soc Lond B* 352(661-668 (1997)

[22] C.-T. Germer, A. Roggan, J. P. Ritz, C. Isbert, D. Albrecht, G. Müller and H. J. Buhr, "Optical properties of native and coagulated human liver tissue and liver metastases in the near infrared range", *Las Surg Med* 23(194-203 (1998)

[23] C. R. Simpson, M. Kohl, M. Essenpreis and M. Cope, "Near-infrared optical properties of ex vivo human skin and subcutaneous tissues measured using the Monte Carlo inversion technique", *Phys Med Biol* 43 (2485-2478 (1998)

[24] J. W. Li, M. K. Karmakar, X. Li, W. H. Kwok and W. D. N. Kee, "Gelatin-Agar Lumbosacral Spine Phantom", *J Ultrasound Med* 30(263-272 (2011)

[25] D. W. Rickey, P. A. Picot, D. A. Christopher and A. Fenster, "A wall-less vessel phantom for Doppler ultrasound studies", *Ult Med Biol* 21(9), 1163-1176 (1995)

[26] M. Jaeger, S. Schüpbach, A. Gertsch, M. Kitz and M. Frenz, "Fourier reconstruction in optoacoustic imaging using truncated regularized inverse k-space interpolation", *Inverse Probl.* 23(6), S51-S63 (2007)

[27] M. Jaeger, M. Frenz and D. Schweizer, "Iterative reconstruction algorithm for reduction of echo background in optoacoustic images", *Photons Plus Ultrasound: Imaging and Sensing* 6856, 68561C-1-15 (2008)

[28] T. Shiina, N. Nitta, E. Ueno, SJSUM and J. C. Bamber, "Real time tissue elasticity imaging using the combined autocorrelation method", *J Med Ultrasonics* 26(2), 57-66 (2002)

[28a] Jacques S L. Light distributions from point, line and plane sources for photochemical reactions and fluorescence in turbid biological tissues. Photochem Photobiol. 67(1):23-32 (1998)

[29] G. M. Spirou, A. A. Oraevsky, I. A. Vitkin and W. M. Whelan, "Optical and acoustic properties at 1064 nm of polyvinyl chloride-plastisol for use as a tissue phantom in biomedical optoacoustics", *Phys. Med. Biol.* 50(N141-N153 (2005)

[30] K. F. Palmer and D. Williams, "Optical properties of water in the near infrared", *J Opt Soc Am* 64(8), 1107-1110 (1974)

[31] M. Jaeger, D. Harris-Birtill, N. L. Bush, A. Gertsch, E. O'Flynn and J. Bamber, "Clinical feasibility of duplex photoacoustic and ultrasound imaging using photoacoustic transmit waves", *Ult Med Biol* submitted ((2012)

[32] Safety of laser products. Equipment classification and requirements. BS EN 60825-1:2007. British Standards Institution (2007)

The invention claimed is:

1. A method of imaging a region of interest of a body, the body having sites outside the region which can produce image clutter, the method including: generating a first pattern of vibration within the body to produce a localized first displacement at the region and localized first displacements at the clutter-producing sites; while the body undergoes the first displacements, generating ultrasound signals from the region, and detecting the ultrasound signals to generate a first photoacoustic emission amplitude or ultrasound echo amplitude image of the region; generating a second pattern of vibration within the body to produce a localized second displacement at the region and localized second displacements at the clutter-producing sites; while the body undergoes the second displacements, generating ultrasound signals from the region, and detecting the ultrasound signals to generate a second photoacoustic emission amplitude or ultrasound echo amplitude image of the region; and combining the first and second images to produce a third photoacoustic emission amplitude or ultrasound echo amplitude image of the region; wherein the first and second vibration patterns are selected and the first and second images are combined in the production of the third image to reduce or eliminate the clutter in the third image relative to the clutter in the first and second images, and to produce the third image so that original amplitudes of the first and/or second images can be obtained from the third image.

2. A method according to claim 1, which is a method of photoacoustic imaging, the ultrasound signals being generated from the region by optically irradiating the region using light.

3. A method according to claim 1, in which the third image produced by combining the first and second images is a difference image.

4. A method according to claim 1, in which the first and the second images are each generated by combining a plurality of sequentially acquired image frames.

5. A method according to claim 4, wherein, during their sequential acquisition, the image frames of the first image are interleaved with the image frames of the second image.

6. A method according to claim 1, further including:
generating one or more further patterns of vibration within the body to produce, for each further pattern, a localized further displacement at the region and localized further displacements at the clutter-producing sites;
while the body undergoes the further displacements of each further vibration pattern, generating ultrasound signals from the region, and detecting the ultrasound signals to generate a respective further photoacoustic emission amplitude or ultrasound echo amplitude image of the region for each further vibration pattern; and
combining the one or more further images with the first and second images to produce the third image of the region.

7. A method according to claim 1, further including:
measuring the vector(s) of the localized displacement(s) produced by each vibration pattern.

8. A method according to claim 1, in which each vibration pattern is generated by the acoustic radiation force of a focused ultrasonic beam.

9. A method according to claim 1, in which the same ultrasound imaging probe is used to detect the ultrasound signals as is used to generate the respective vibration pattern.

10. A method according to claim 1, further comprising:
repeatedly performing the generating and detecting steps for different regions of interest of the body; and
combining the third images from the repeated performances to build up a composite image of the body.

11. A method according to claim 10, wherein, in the repeated performances, the detected ultrasound signals used to generate an image of one region are reused to generate images of one or more additional regions.

12. A method of imaging a region of interest of a body, the body having sites outside the region which can produce image clutter, the method including: generating a pattern of vibration within the body to produce a non-zero localized displacement at a first location which is one of (A) the region and (B) the clutter-producing sites and no displacement at a second location which is the other of (A) the region and (B) the clutter-producing sites; while the first location undergoes the displacement, generating ultrasound signals from the region, and detecting the ultrasound signals to generate a first photoacoustic emission amplitude or ultrasound echo amplitude image of the region; in the absence of displacement at the region and the clutter-producing sites, generating ultrasound signals from the region, and detecting the ultrasound signals to generate a second photoacoustic emission amplitude or ultrasound echo amplitude image of the region; combining the first and second images to produce a third photoacoustic emission amplitude or ultrasound echo amplitude image of the region, the clutter in the third image being reduced or eliminated relative to the clutter in the first and second images, and the third image being produced so that original amplitudes of the first and/or second images can be obtained from the third image.

13. A method according to claim 12 which is a method of photoacoustic imaging, the ultrasound signals being generated from the region by optically irradiating the region using light.

14. A method according to claim 12 in which the third image produced by combining the first and second images is a difference image.

15. A method according to claim 12 in which the first and the second images are each generated by combining a plurality of sequentially acquired image frames.

16. A method according to claim 15, wherein, during their sequential acquisition, the image frames of the first image are interleaved with the image frames of the second image.

17. A method according to claim 12 further including:
generating one or more further patterns of vibration within the body to produce, for each further pattern, a localized further displacement at the region and localized further displacements at the clutter-producing sites;

while the body undergoes the further displacements of each further vibration pattern, generating ultrasound signals from the region, and detecting the ultrasound signals to generate a respective further photoacoustic emission amplitude or ultrasound echo amplitude image of the region for each further vibration pattern; and combining the one or more further images with the first and second images to produce the third image of the region.

18. A method according to claim 12 further including:
measuring the vector(s) of the localized displacement(s) produced by the vibration pattern.

19. A method according to claim 12, in which the vibration pattern is generated by the acoustic radiation force of a focused ultrasonic beam.

20. A method according to claim 12, in which the same ultrasound imaging probe is used to detect the ultrasound signals as is used to generate the respective vibration pattern.

21. A method according to claim 12, further comprising:
repeatedly performing the generating and detecting steps for different regions of interest of the body; and
combining the third images from the repeated performances to build up a composite image of the body.

22. A method according to claim 21, wherein, in the repeated performances, the detected ultrasound signals used to generate an image of one region are reused to generate images of one or more additional regions.

23. A system for imaging a region of interest of a body, the body having sites outside the region which can produce image clutter, the system including: (i) an apparatus for: (a) generating a pattern of vibration within the body to produce a localized displacement at the region and localized displacements at the clutter-producing sites, (b) while the body undergoes the displacements, generating ultrasound signals from the region, and (c) detecting the ultrasound signals to generate photoacoustic emission amplitude or ultrasound echo amplitude image of the region; and (ii) a computer system which controls the apparatus to: either (a) generate a first pattern of vibration within the body to produce a localized first displacement at the region and localized first displacements at the clutter-producing sites; while the body undergoes the first displacements, generate ultrasound signals from the region, and detect the ultrasound signals to generate a first photoacoustic emission amplitude or ultrasound echo amplitude image of the region; generate a second pattern of vibration within the body to produce a localized second displacement at the region and localized second displacements at the clutter-producing sites; while the body undergoes the second displacements, generate ultrasound signals from the region, and detect the ultrasound signals to generate a second photoacoustic emission amplitude or ultrasound echo amplitude image of the region; or (b) generate a pattern of vibration within the body to produce a non-zero localized displacement at a first location which is one of (A) the region and (B) the clutter-producing sites and no displacement at a second location which is the other of (A) the region and (B) the clutter-producing sites; while the first location undergoes the displacement, generate ultrasound signals from the region, and detect the ultrasound signals to generate a first photoacoustic emission amplitude or ultrasound echo amplitude image of the region; in the absence of displacement at the region and the clutter-producing sites, generate ultrasound signals from the region, and detect the ultrasound signals to generate a second photoacoustic emission amplitude or ultrasound echo amplitude image of the region; wherein the computer system further combines the first and second images to produce a third photoacoustic emission amplitude or ultrasound echo amplitude image of the region, the clutter in the third image being reduced or eliminated relative to the clutter in the first and second images, and the third image being produced so that original amplitudes of the first and/or second images can be obtained from the third image.

24. A non-transient computer readable medium storing a computer program comprising code which, when run on a computer, causes the computer to control an apparatus for (a) generating a pattern of vibration within the body to produce a localized displacement at the region and localized displacements at the clutter-producing sites, (b) while the body undergoes the displacements, generating ultrasound signals from the region, and (c) detecting the ultrasound signals to generate photoacoustic emission amplitude or ultrasound echo amplitude image of the region; the computer program controlling the apparatus to: either (a) generate a first pattern of vibration within the body to produce a localized first displacement at the region and localized first displacements at the clutter-producing sites; while the body undergoes the first displacements, generate ultrasound signals from the region, and detect the ultrasound signals to generate a first photoacoustic emission amplitude or ultrasound echo amplitude image of the region; generate a second pattern of vibration within the body to produce a localized second displacement at the region and localized second displacements at the clutter-producing sites; while the body undergoes the second displacements, generate ultrasound signals from the region, and detect the ultrasound signals to generate a second photoacoustic emission amplitude or ultrasound echo amplitude image of the region; or (b) generate a pattern of vibration within the body to produce a non-zero localized displacement at a first location which is one of (A) the region and (B) the clutter-producing sites and no displacement at a second location which is the other of (A) the region and (B) the clutter-producing sites; while the first location undergoes the displacement, generate ultrasound signals from the region, and detect the ultrasound signals to generate a first photoacoustic emission amplitude or ultrasound echo amplitude image of the region; in the absence of displacement at the region and the clutter-producing sites, generate ultrasound signals from the region, and detect the ultrasound signals to generate a second photoacoustic emission amplitude or ultrasound echo amplitude image of the region; wherein the computer program further comprises code which combines the first and second images to produce a third image of the region, the clutter in the third image being reduced or eliminated relative to the clutter in the first and second images, and the third image being produced so that original amplitudes of the first and/or second images can be obtained from the third image.

25. A method of imaging a region of interest of a body, the body having sites outside the region which can produce image clutter, and the body undergoing autonomous tissue motion which produces a localized first displacement at the region and localized first displacements at the clutter-producing sites, and which further produces a localized second displacement at the region and localized second displacements at the clutter-producing sites, the method including:
while the body undergoes the first displacements, generating ultrasound signals from the region, and detecting the ultrasound signals to generate a first photoacoustic emission amplitude or ultrasound echo amplitude image of the region; while the body undergoes the second displacements, generating ultrasound signals from the region, and detecting the ultrasound signals to generate a second photoacoustic emission amplitude or ultrasound echo amplitude image of the region; and combining the first and second images to produce a third photoacoustic emission amplitude or ultrasound echo amplitude image of the region; wherein the first and second vibration patterns are selected and the first and second images are combined in the production of the third image to reduce or eliminate the clutter in the third image relative to the clutter in the first and second images, and to produce the third image so that original amplitudes of the first and/or second images can be obtained from the third image.

26. A method according to claim 25, wherein the autonomous tissue motion is artery pulsation.

\* \* \* \* \*